(12) United States Patent
Kim et al.

(10) Patent No.: US 9,546,139 B2
(45) Date of Patent: Jan. 17, 2017

(54) PYRIDINE CARBOXYLIC ACID BASED COMPOUND USED AS A P2X1 AND P2X3 RECEPTOR ANTAGONIST, A PRODUCTION METHOD FOR THE SAME AND A COMPOSITION COMPRISING THE SAME

(75) Inventors: Yong-Chul Kim, Buk-gu Gwangju (KR); Kwan-Young Jung, Buk-gu Gwangju (KR); Joong Heui Cho, Chungcheongbuk-do (KR)

(73) Assignee: GWANGJU INSTITUTE OF SCIENCE AND TECHNOLOGY, Buk-gu, Gwangju (KR)

( * ) Notice: Subject to any disclaimer, the term of this patent is extended or adjusted under 35 U.S.C. 154(b) by 711 days.

(21) Appl. No.: 13/643,674

(22) PCT Filed: Dec. 20, 2010

(86) PCT No.: PCT/KR2010/009096
§ 371 (c)(1),
(2), (4) Date: Oct. 26, 2012

(87) PCT Pub. No.: WO2011/136459
PCT Pub. Date: Nov. 3, 2011

(65) Prior Publication Data
US 2013/0040997 A1    Feb. 14, 2013

(30) Foreign Application Priority Data

Apr. 26, 2010  (KR) .................. 10-2010-0038535

(51) Int. Cl.
| C07D 213/79 | (2006.01) |
|---|---|
| C07D 213/77 | (2006.01) |
| C07D 213/80 | (2006.01) |
| C07D 213/65 | (2006.01) |
| C07D 213/66 | (2006.01) |

(52) U.S. Cl.
CPC .......... *C07D 213/77* (2013.01); *C07D 213/65* (2013.01); *C07D 213/66* (2013.01); *C07D 213/79* (2013.01); *C07D 213/80* (2013.01)

(58) Field of Classification Search
CPC ... C07D 211/38; C07D 213/65; C07D 213/66; C07D 213/77; C07D 213/79; C07D 213/80
USPC ................................. 546/314, 326
See application file for complete search history.

(56) References Cited

U.S. PATENT DOCUMENTS 4,206,117 A * 6/1980 Von Philipsborn .. A61C 8/0018
514/210.2

OTHER PUBLICATIONS

Chatterjea et al. "Syntheses in the 3-azafluorene . . . " CA54:128990 (1960).*
Boell et al. "Pyridinyl amino . . . " CA90:103838 (1979).*
Kawazu et al. "3-hydroxypyridines" CA74:99885 (1971).*
Tsitini-Tsami et al. "Special feature . . . " CA95:114464 (1981).*
Exhibit A "core search" p. 1 (2015).*

* cited by examiner

*Primary Examiner* — Celia Chang
(74) *Attorney, Agent, or Firm* — Nath, Goldberg & Meyer; Joshua B. Goldberg; Tanya E. Harkins

(57) ABSTRACT

Provided are a novel pyridine carboxylic acid based compound used as a $P2X_1$ and $P2X_3$ receptor antagonist, a production method for the same and a composition comprising the same. The compound according to the present invention is a powerful antagonist of $P2X_1$ and $P2X_3$ receptors, and hence can be used as a drug for treating or preventing diseases involving neurological pain or chronic inflammatory diseases which are diseases caused by $P2X_1$ and $P2X_3$ receptor activity.

11 Claims, 2 Drawing Sheets

PYRIDINE CARBOXYLIC ACID BASED COMPOUND USED AS A P2X1 AND P2X3 RECEPTOR ANTAGONIST, A PRODUCTION METHOD FOR THE SAME AND A COMPOSITION COMPRISING THE SAME

This is a National Phase Application filed under 35 U.S.C. 371 as a national stage of PCT/KR2010/009096, filed Dec. 20, 2010, and claims priority from Korean Application No. 10-2010-0038535, filed Apr. 26, 2010, the content of each of which is hereby incorporated by reference in its entirety.

FIELD OF THE INVENTION

The present invention relates to novel pyridine carboxylic acid based compound served as a $P2X_1$ and $P2X_3$ receptor antagonist, a production method for the same and a composition comprising the same.

DESCRIPTION OF THE RELATED ART

[Reference 1] Burnstock, G., Purinergic P2 receptors as targets for novel analgesics. Pharmacol Ther 2006, 110 (3), pp. 433-54.
[Reference 2] Communi, D.; Boeynaems, J. M., Receptors responsive to extracellular pyrimidine nucleotides. Trends Pharmacol. Sci. 1997, 18(3), pp. 83-6.
[Reference 3] Illes, P.; Ribeiro, J. A., Neuronal P2 receptors of the central nervous system. Curr. Top Med. Chem. 2004, 4(8), pp. 831-8.
[Reference 4] Burnstock, G., et al. Purine-mediated signalling in pain and visceral perception. Trends Pharmacol. Sci. 2001, 22(4), pp. 182-8.
[Reference 5] Vial, C.; Roberts, J. A.; Evans, R. J., Molecular properties of ATP-gated P2X receptor ion channels. Trends Pharmacol. Sci. 2004, 25(9), pp. 487-93.
[Reference 6] Jarvis, M. F., Contributions of P2X3 homomeric and heteromeric channels to acute and chronic pain. Expert Opin. Ther. Targets 2003, 7(4), pp. 513-22.
[Reference 7] Dunn, P. M.; Zhong, Y.; Burnstock, G., P2X receptors in peripheral neurons. Prog. Neurobiol. 2001, 65(2), pp. 107-34.
[Reference 8] Burgard, E. C.; Niforatos, W.; van Biesen, T.; Lynch, K. J.; Touma, E.; Metzger, R. E.; Kowaluk, E. A.; Jarvis, M. F., P2X receptor-mediated ionic currents in dorsal root ganglion neurons. J. Neurophysiol. 1999, 82(3), pp. 1590-8.
[Reference 9] Gever, J. R.; Cockayne, D. A.; Dillon, M. P.; Burnstock, G.; Ford, A. P., Pharmacology of P2X channels. Pflugers Arch. 2006, 452(5), pp. 513-37.
[Reference 10] Honore, P.; Mikusa, J.; Bianchi, B.; McDonald, H.; Cartmell, J.; Faltynek, C.; Jarvis, M. F., TNP-ATP, a potent P2X3 receptor antagonist, blocks acetic acid-induced abdominal constriction in mice: comparison with reference analgesics. Pain 2002, 96 (1-2), pp. 99-105.
[Reference 11] Jarvis, M. F.; Burgard, E. C.; McGaraughty, S.; Honore, P.; Lynch, K.; Brennan, T. J.; Subieta, A.; Van Biesen, T.; Cartmell, J.; Bianchi, B.; Niforatos, W.; Kage, K.; Yu, H.; Mikusa, J.; Wismer, C. T.; Zhu, C. Z.; Chu, K.; Lee, C. H.; Stewart, A. O.; Polakowski, J.; Cox, B. F.; Kowaluk, E.; Williams, M.; Sullivan, J.; Faltynek, C., A-317491, a novel potent and selective non-nucleotide antagonist of P2X3 and P2X2/3 receptors, reduces chronic inflammatory and neuropathic pain in the rat. Proc. Natl. Acad. Sci. USA 2002, 99(26), pp. 17179-84.
[Reference 12] Jung, K. Y.; Moon, H. D.; Lee, G. E.; Lim, H. H.; Park, C. S.; Kim, Y. C., Structure-activity relationship studies of spinorphin as a potent and selective human P2X(3) receptor antagonist. J. Med. Chem. 2007, 50(18), pp. 4543-7.
[Reference 13] Christine E. Brotherton-Pleiss, Michael P. Dillon, Anthony P. D. W. Ford, Joel R. Gever, David S. Carter, Shelley K. Gleason, Clara J. Lin, Amy G. Moore, Anthony W. Thompson, Marzia Villa, Yansheng Zhai. Discovery and optimization of RO-85, a novel drug-like, potent, and selective P2X3 receptor antagonist Bioorg. Med. Chem. Lett. 2010, 20, pp. 1031-1036.
[Reference 14] Kim, Y. C.; Brown, S. G.; Harden, T. K.; Boyer, J. L.; Dubyak, G.; King, B. F.; Burnstock, G.; Jacobson, K. A., Structure-activity relationships of pyridoxal phosphate derivatives as potent and selective antagonists of P2X1 receptors. J. Med. Chem. 2001, 44(3), pp. 340-9.
[Reference 15] Michal F. Jarvis. The neural-glial purinergic receptor ensemble in chronic pain states. Trends in Neurosci. 2009, 33(1), pp. 48-57.
[Reference 16] Oury C, Toth-Zsamboki E, Vermylen J. et al. P2X1-mediated activation of extracellular signal-regulated kinase 2 contributes to platelet secretion and aggrefation induced by collagen. Blood, 2002, 100, pp. 2499-2505
[Reference 17] Chales kennedy. P2X Receptors: Targets for novel analgesics?. The neuroscientist 2005, 11, pp. 345-56.
[Reference 18] Song-Yi Lee, Sooyeon Jo, Ga Eun Lee, Lak Shin Jeong, Yong-Chul Kim, and CHul-seung Park. Establishment of an assay for P2X7 receptor-mediated cell death. Mol. Cells, 2006, 22, pp. 198-202.
[Reference 19] Harald Schmalwasser, Andreas Neef, Alison A. Elliott, Stefan H. Heinemann. Two-electrode voltage clamp of Xenopus oocytes under high hydrostatic pressure. J. Neurosci. Methods, 1998, 81, pp. 1-7.

DETAILED DESCRIPTION OF THIS INVENTION

Technical Purposes of this Invention

Extracellular ATP (adenosine 5'-triphosphate) plays a distinct role in pain transmission or inflammatory signaling through P2 receptor activation, acting on various cells and organs including nerve, muscle, heart, kidney and immune system (Burnstock, G., et al, 2006). The P2 nucleotide receptor has three families. P2X receptor is known as ligand-gated cation channel family and P2Y receptor is known as G-protein coupled receptor family (Communi, D. et al, 1997).

The P2Y receptor has at least ten subtypes derived from $P2Y_1$, $P2Y_6$, $P2Y_{11}$, $P2Y_{12}$, $P2Y_{13}$ and $P2Y_{14}$ which are detected in CNS (Illes, P. et al, 2004).

The P2Y receptor plays a significant role in the function of peripheral nervous system and central nervous system by stimulation generation in primary afferent nerve and synaptic adjustment (Burnstock, G., et al, 2001). Currently, seven human P2X receptor subtypes ($P2X_{1-7}$) have been cloned. They display 30-50% sequence homology in the protein level and have 379-595 amino acids in length. The P2X receptor subunits have structural topologic similarity and consist of two transmembrane spanning domains (TM1 and TM2) which are linked by long extracellular loop including intracellular ATP binding site and various lengths of intracellular N-terminus and intracellular C-terminus ATP-binding site (Vial, C. et al, 2004).

Homomeric $P2X_3$ and heteromeric $P2X_{2/3}$ receptors are known to play a major role in mediating the primary sensory effects of ATP (Jarvis, M F, et al, 2003), which are mainly localized in small-medium size of C-fibers and Aδ sensory neurons of dorsal root, trigeminal and nodose sensory ganglia (Dunn, P. M. et, 2001). In electrophysiological study with sensory neurons from $P2X_2$ and $P2X_3$ deficient mouse, $P2X_2$ and $P2X_3$ receptors are responsible all ATP reaction of DRG sensory neurons even P2X$_2$ and P2X$_3$ receptors are mainly distributed in the nodular (nodose) ganglion (Burgard, E. C. et al., 1999).

P2X$_2$ and P2X$_{2/3}$ receptors exist in all of peripheral and the central terminal of primary sensory afferents which spread to somatosensory, skin, joint, bone, lung, bladder, ureter and internal organs including gastrointestinal tract (Geyer, J. R. et al, 2006).

In recently study, it is known that epithelial cells including bladder epithelium, tracheal epithelium and pulmonary nervous epithelium express P2X$_2$ and P2X$_{2/3}$ channel, in which regulate particular mechanical sensory or chemical sensory response (Wang, E. C. et al. 2005).

Since antagonists powerful and selective to P2X receptors have therapeutic potential, studies have been made for conventional pharmaceutic activators such as (1) TNP-ATP in P2X$_1$, P2X$_3$ and P2X$_{2/3}$ receptors (Honore, P. et al, 2002), (2) A-317491 in P2X$_3$ and P2X$_{2/3}$ receptors (Jarvis, M F et al, 2002), (3) Spinorphin in P2X$_3$ receptor (Jung, K Y et al, 2007) and (4) RO-85 in P2X$_3$ receptors (Roche Co., Brotherton-Pleiss, C E et al, 2009).

In the present invention, it has been elucidated that peripheral and spinal P2X$_3$ and P2X$_{2/3}$ receptors are associated with persistent and chronic inflammatory and neuropathic pain signaling. Another type of P2 receptor antagonists, PPADS (pyridoxalphosphate-6-azophenyl-2',4'-disulfonic acid) and its derivatives have IC$_{50}$ values in nanomolar ranges, selectivity for P2Y$_1$ receptor and turned out to be a powerful antagonist on P2X$_{1, 3}$ receptor (Kim, Y C et al, 2001).

P2X$_1$ and P2X$_3$ receptors have been reported to be directly related with chronic inflammatory diseases (Michael, F. et al, 2009), platelet disorders (Oury, C. et al, 2002) or neuropathic pain disease (Charles, Kennedy et al, 2005).

However, no reference mentioned above discloses or describes that pyridine carboxylic acid-based compounds may be used as antagonist to P2X$_1$ and P2X$_3$ receptors.

The present inventors have prepared carboxylic acid derivatives of pyridoxal or pyridoxic acid to finally develop 6-arylalkyl pyridine derivatives containing carboxylic acid side chain instead of strong anionic phosphate by replacing unstable azo group with stable carbon-carbon chain (chemical formula of pyridoxal-5-phosphate and chemical formula of its azo-based derivatives (PPADS, iso-PPADS) and MRS compounds, see the following chemical formulae).

[Chemical formula 1]

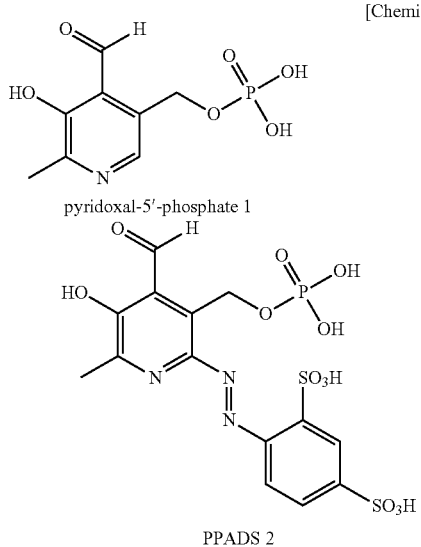

pyridoxal-5'-phosphate 1

PPADS 2

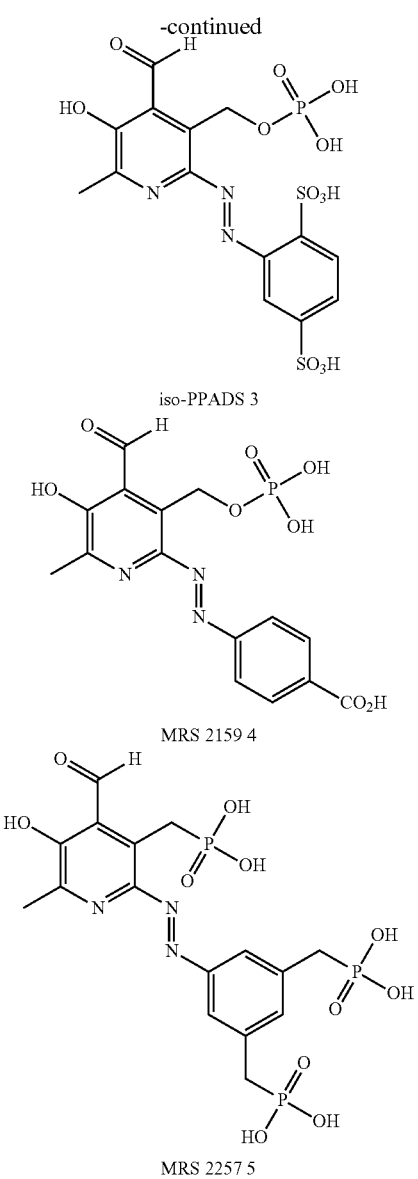

iso-PPADS 3

MRS 2159 4

MRS 2257 5

The present inventors have prepared novel pyridine carboxylic acid-based compounds and elucidated their powerful antagonistic activity to P2X$_1$ and P2X$_3$ receptors using two-electrode voltage clamp (TEVC) assay in *Xenopus* oocyte expressing mouse P2X$_1$ receptor and human P2X$_3$ receptor. As results, the present inventors have revealed that the present compounds have higher applicability as drugs for treating or preventing chronic inflammatory diseases or neuropathic pain diseases caused by P2X$_1$ and P2X$_3$ receptor activity.

Throughout this application, several patents and publications are referenced and citations are provided in parentheses. The disclosure of these patents and publications is incorporated into this application in order to more fully describe this invention and the state of the art to which this invention pertains.

SUMMARY OF THE INVENTION

It is an object of this invention to provide novel pyridine carboxylic acid-based compound used as a P2X$_1$ and P2X$_3$ receptor antagonist, a production method for the same and a composition comprising the same.

It is another object of this invention to provide a method for preventing or treating chronic inflammatory disease, neurological pain disease or platelet aggregation-associated disease caused by $P2X_1$ and $P2X_3$ receptor activity.

Other objects and advantages of the present invention will become apparent from the detailed description to follow taken in conjugation with the appended claims and drawings.

DETAILED DESCRIPTION OF THIS INVENTION

Figure 1:
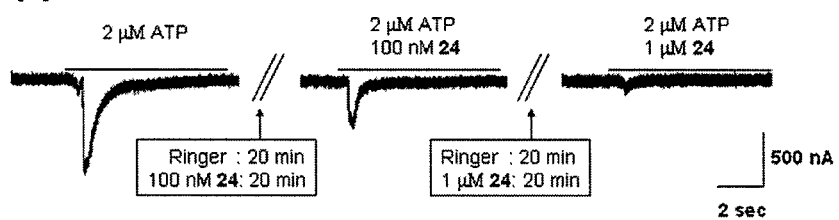
FIG. 1A shows inhibition of mouse $P2X_1$ receptor-mediated currents by the compound 24. Representative inward current elicited by 2 μM ATP in control and in the presence of two concentrations of the compound 24, in *Xenopus* oocytes expressing mouse $P2X_1$ receptor subtype (A).
FIGS. 1B and 1C show the concentration-inhibitory curves of the compound 24 (■), 28 (●) and iso-PPADS 3 (▲) for mouse $P2X_1$ receptor (B) and human $P2X_3$ receptor (C). The continuous line for ATP is fit to the data using the equation: $I=I_{max}/(1+IC_{50}/L)^{nH}$, where I is the actual current for a ligand concentration (L), nH is the Hill coefficient and $I_{max}$ is the maximal current.
Figure 1:
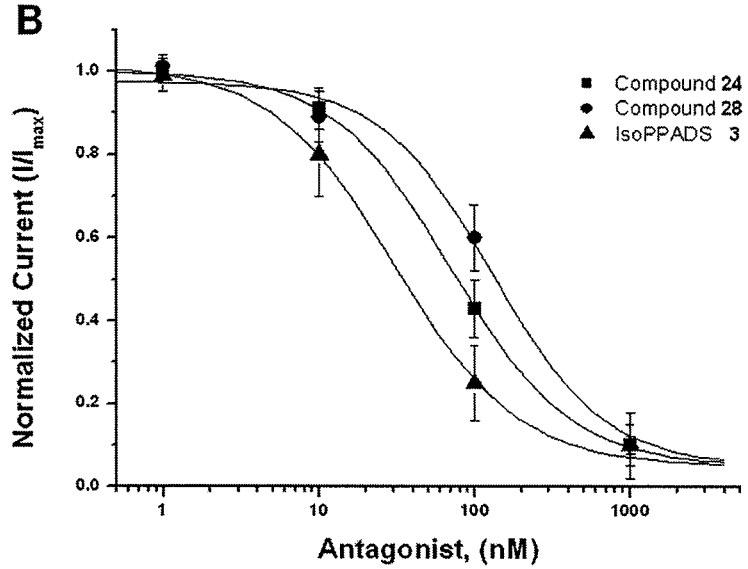
Figure 1:
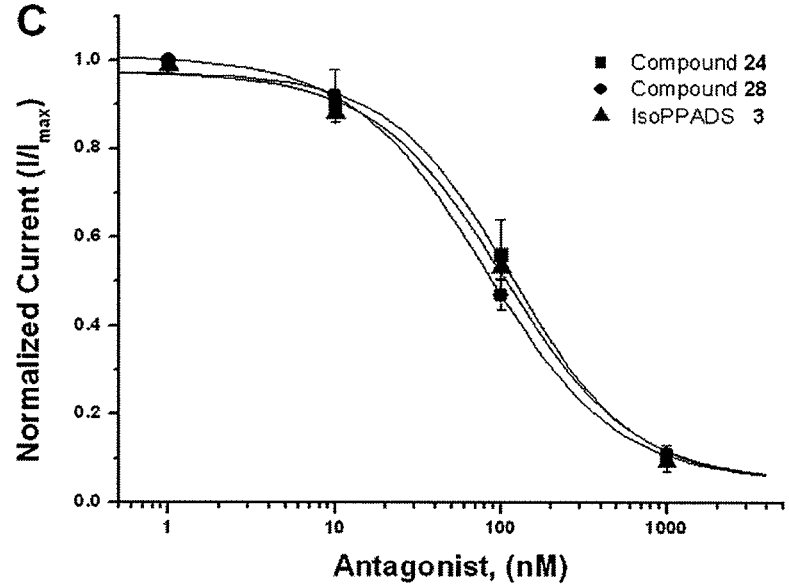

In one aspect of the present invention, there is provided a pyridine carboxylic acid-based compound represented by the General formula (I) having an antagonistic activity to P2X1 and P2X3 receptors, isomers or pharmaceutically acceptable salt thereof:

[Chemical formula 2]

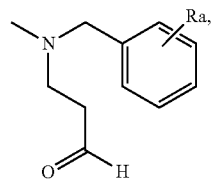

(I)

wherein, each of $R_1$, $R_2$ and $R_3$ is a substituent independently selected from the group consisting of hydrogen, hydroxy group, sulfonyl group, halogen, carboxylic acid, $C_1$-$C_6$ lower alkyl group, $C_1$-$C_6$ lower alkoxy group and $C_1$-$C_6$ lower alkyl ester group;

A is

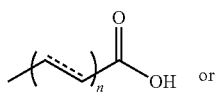

(A1)

or

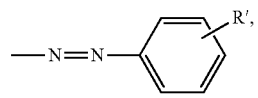

(A2)

wherein, n is an integer of 0 to 5 and Ra is at least one substituent selected from the group consisting of hydrogen, hydroxy group, halogen, carboxylic acid, $C_1$-$C_6$ lower alkyl group, $C_1$-$C_6$ lower alkoxy group and $C_1$-$C_6$ lower alkyl ester group;

B is

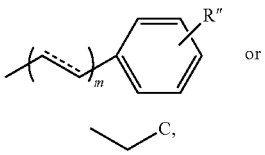

(B1)

(B2)

(B3)

wherein, each of R' and R" is at least one substituent selected from the group consisting of hydrogen, hydroxy group, halogen, carboxylic acid, sulfonyl group, $C_1$-$C_6$ lower alkyl group, $C_1$-$C_6$ lower alkoxy group and $C_1$-$C_6$ lower alkyl ester group, C is at least one 5-18 membered aromatic ring, m is an integer of 0 to 5 and (----) represents a single or double bond.

According to a preferred embodiment, wherein each of $R_1$, $R_2$ and $R_3$ in the General formula (I) is a substituent selected from the group consisting of hydrogen, hydroxy group, sulfonyl group, $C_1$-$C_3$ lower alkyl group and $C_1$-$C_3$ lower alkoxy group; wherein n is an integer of 0 to 2, provided that A is A1; wherein Ra is at least one substituent selected from the group consisting of hydrogen, hydroxy group and halogen, provided that A is A2; wherein R' and R" are at least one substituent selected from the group consisting of hydrogen, hydroxy group, halogen, carboxylic acid, sulfonyl group, $C_1$-$C_3$ lower alkyl group, $C_1$-$C_3$ lower alkoxy group and $C_1$-$C_6$ lower alkyl ester group and m is an integer of 0 to 2, provided that B is B1 or B2; wherein C is at least one 6-12 membered aromatic ring, provided that B is B3.

In another aspect of the present invention, there is provided a pyridine carboxylic acid-based compound represented by the General formula (Ia) having an antagonistic activity to $P2X_1$ and $P2X_3$ receptors, isomers or pharmaceutically acceptable salt thereof:

[Chemical formula 3]

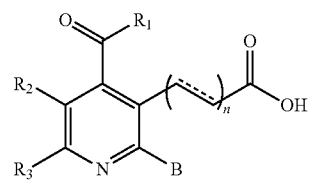

(Ia)

wherein, $R_1$, $R_2$, $R_3$, B and n have the same meaning as the above General formula (I).

In still another aspect of the present invention, there is provided a pyridine carboxylic acid-based compound represented by the General formula (Ib) having an antagonistic activity to $P2X_1$ and $P2X_3$ receptors, isomers or pharmaceutically acceptable salt thereof:

[Chemical formula 4]

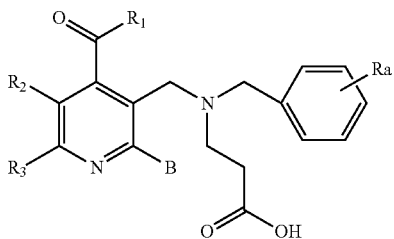

(Ib)

wherein, $R_1$, $R_2$, $R_3$ and B have the same meaning as the above General formula (I).

In still another aspect of the present invention, there is provided a pyridine carboxylic acid-based compound represented by the General formula (Ic) having an antagonistic activity to $P2X_1$ and $P2X_3$ receptors, isomers or pharmaceutically acceptable salt thereof:

[Chemical formula 5]

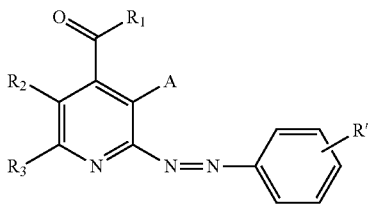

(Ic)

wherein, $R_1$, $R_2$, $R_3$, R' and A have the same meaning as the above General formula (I).

In still another aspect of the present invention, there is provided a pyridine carboxylic acid-based compound represented by the General formula (Id) having an antagonistic activity to $P2X_1$ and $P2X_3$ receptors, isomers or pharmaceutically acceptable salt thereof:

[Chemical formula 6]

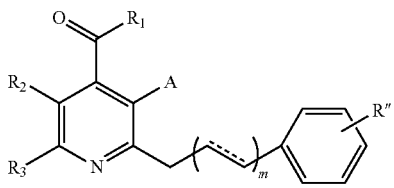

(Id)

wherein, $R_1$, $R_2$, $R_3$, R", m and A have the same meaning as the above General formula (I).

In still another aspect of the present invention, there is provided a pyridine carboxylic acid-based compound represented by the General formula (Ie) having an antagonistic activity to $P2X_1$ and $P2X_3$ receptors, isomers or pharmaceutically acceptable salt thereof:

[Chemical formula 7]

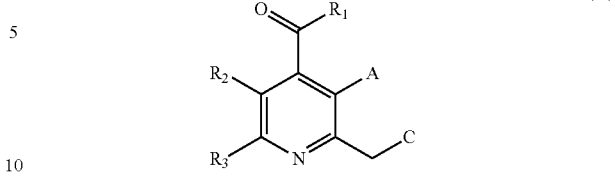

(Ie)

wherein, $R_1$, $R_2$, $R_3$, R", A and C have the same meaning as the above General formula (I).

According to a preferred embodiment, each of $R_1$, $R_2$ and $R_3$ in the General formula (Ia)-(Ie) is a substituent selected from the group consisting of hydrogen, hydroxy group, sulfonyl group, methyl group, ethyl group, methoxy group and ethoxy group; wherein n is an integer of 0 or 1, provided that A is A1; wherein Ra is at least one substituent selected from the group consisting of hydrogen and hydroxy group, provided that A is A2; wherein the R' and the R" are at least one substituent selected from the group consisting of hydrogen, hydroxy group, carboxylic acid, sulfonyl group, methyl group, ethyl group, methoxy group and ethoxy group and m is an integer of 0 or 1, provided that B is B1 or B2; wherein C is one or two membered aromatic ring selected from the group consisting of phenyl group, naphthalene group, phenoxy phenyl group, adamantine group, pyrazine group, tetrazole group, indole group, anthracene group, piperidine group, quinoline group, isoquinoline group, quinazoline group, benzazepine group, pyridine group, pyridazine group, pyrazole group, oxazole group, thiazole group or adenine group, provided that B is B3.

Among the compounds represented by the General formulae (Ia)-(1e), the compounds represented by the General formula (Ia) preferably comprise ethyl 3-(4-formyl-5-hydroxy-6-methylpyridin-3-yl) propanoic acid (13), 5-(2-carboxyethyl)-3-hydroxy-2-methylisonicotinic acid (14), (3-(2,2,8-trimethyl-4H-[1,3]dioxino[4,5-c]pyridin-5-yl)acrylic acid (15), 3-(5-hydroxy-4-(hydroxymethyl)-6-methylpyridin-3-yl)acrylic acid (16), 3-(4-Formyl-5-hydroxy-6-methylpyridin-3-yl)acrylic acid (17), 5-(2-Carboxyvinyl)-3-hydroxy-2-methylisonicotinic acid (18), N-Benzyl-1-(2,2,8-trimethyl-4H-[1,3]dioxino[4,5-c]pyridin-5-yl)methanamine (19), Ethyl 3-(benzyl((2,2,8-trimethyl-4H-[1,3]dioxino[4,5-c]pyridin-5-yl)methyl)amino)propanoate (20), 3-(Benzyl((5-hydroxy-4-(hydroxymethyl)-6-methylpyridin-3-yl)methyl)amino)propanoic acid (21);

the compounds represented by the General formula (Ib) preferably comprise 3-(Benzyl((4-formyl-5-hydroxy-6-methylpyridin-3-yl)methyl)amino)propanoic acid (22), 5-((Benzyl(2-carboxyethyl)amino)methyl)-3-hydroxy-2-methylisonicotinic acid (23);

the compounds represented by the General formula (Ic) preferably comprise 3-(2-((2,5-Disulfophenyl)diazenyl)-4-formyl-5-hydroxy-6-methylpyridin-3-yl)propanoic acid (24), 3-(2-Carboxyethyl)-2-((2,5-disulfophenyl)diazenyl)-5-hydroxy-6-methylisonicotinic acid (25), 3-(4-Formyl-5-hydroxy-6-methyl-2-((4-sulfophenyl)diazenyl)pyridin-3-yl) propanoic acid (26), 3-(2-carboxyethyl)-5-hydroxy-6-methyl-2-((4-sulfophenyl)diazenyl) isonicotinic acid (27), 4-((3-(2-carboxyethyl)-4-formyl-5-hydroxy-6-methylpyridin-2-yl)diazenyl)benzoic acid (28), 3-(2-carboxyethyl)-2-((4-carboxyphenyl)diazenyl)-5-hydroxy-6-methy lisonicotinic acid (29);

the compounds represented by the General formula (Id) preferably comprise 2-Benzyl-5-hydroxy-6-methyl-pyridine-3,4-dicarboxylic acid (35), 5-Hydroxy-6-methyl-2-phenethyl-pyridine-3,4-dicarboxylic acid (36), 5-Hydroxy-2-[2-(4-methoxy-phenyl)ethyl]-6-methyl-pyridine-3,4- dicarboxylic acid (37), 5-Hydroxy-6-methyl-2-styryl-pyridine-3,4-dicarboxylic acid (38), 2-[2-(4-Carboxy-phenyl)-ethyl]-5-hydroxy-6-methyl-pyridine-3,4-dicarboxylic acid (39), 5-Hydroxy-2-[2-(3-methoxy-phenyl)-ethyl]-6-methyl-pyridine-3,4-dicarboxylic acid (40), 5-Hydroxy-2-[2-(2-methoxy-phenyl)-ethyl]-6-methyl-pyridine-3,4-dicarboxylic acid (41), 4-acetyl-2-benzyl-5-hydroxy-6-methylnicotinic acid (44), 4-acetyl-5-hydroxy-6-methyl-2-phenethylnicotinic acid (45), 4-acetyl-5-hydroxy-2-(4-methoxyphenethyl)-6-methylnicotinic acid (46), (E)-4-acetyl-5-hydroxy-6-methyl-2-styrylnicotinic acid (47), (E)-4-acetyl-5-hydroxy-2-(3-methoxystyryl)-6-methylnicotinic acid (48), (E)-4-acetyl-5-hydroxy-2-(2-methoxystyryl)-6-methylnicotinic acid (49), 3-(4-formyl-5-hydroxy-2-(4-methoxyphenethyl)-6-methylpyridin-3-yl)propanoic acid (61), (E)-3-(4-formyl-5-hydroxy-2-(4-methoxyphenethyl)-6-methylpyridin-3-yl)acrylic acid (64), 4-formyl-5-hydroxy-2-(4-methoxyphenethyl)-6-methylnicotinic acid (67);

the compounds represented by the General formula (Ie) preferably comprise 5-Hydroxy-6-methyl-2-(naphthalene-1-ylmethyl)pyridine-3,4-dicarboxylic acid (50) and 2-(2,2,-diphenylethyl)-5-hydroxy-6-methylpyridine-3,4-dicarboxylic acid (51).

The compounds of the present invention represented by the General formula (I) may be prepared to pharmaceutically acceptable salts and solvates in accordance with conventional methods known in the art.

Acid addition salts formed by pharmaceutically acceptable free acid are useful. The acid addition salts may be prepared using conventional methods. For example, the compound is dissolved in excess of acid and this salt is prepared by precipitation using water-miscible organic solvent such as methanol, ethanol, acetone or acetonitrile. Acid or alcohol (for example, glycol monomethylether) in same molar amount of the compound and water are heated and the mixture is dried by evaporation or the precipitated salts are filtered with suction.

At this time, organic acids and inorganic acids may be used. The inorganic acids may use hydrochloric acid, phosphoric acid, sulfuric acid, nitric acid or tartaric acid. The organic acids may use methane sulfonic acid, p-toluene sulfonic acid, acetic acid, trifluoroacetic acid, citric acid, maleic acid, succinic acid, oxalic acid, benzoic acid, tartaric acid, fumaric acid, mandelic acid, propionic acid, citric acid, lactic acid, glycollic acid, gluconic acid), galacturonic acid, glutamic acid, glutaric acid, glucuronic acid, aspartic acid, ascorbic acid, carbonic acid, vanillic acid or hydroiodic acid.

In addition, pharmaceutically acceptable metal salts may be prepared using base. Alkali metal or alkaline earthmeter salts may be prepared using conventional methods. For example, the compound is dissolved in excess of alkali metal hydroxides or alkaline earthmeter salts hydroxides and after filtration of undissolved compound salts, the resultant is obtained by evaporation and drying. At this time, preparing sodium, potassium or calcium salts are suitable for metal salts in pharmaceuticals and the corresponding silver salts are obtained by being reacted alkali metal or alkaline earthmeter salts with suitable silver salt (for example, silver nitrate).

Unless otherwise noted, pharmaceutically acceptable salt of pyridine carboxylic acid-based compound represented by the General formula (I) comprise acidic or basic salts which may be present in pyridine carboxylic acid-based compound having structure of the General formula (I). For example, pharmaceutically acceptable salts include hydroxyl group of sodium, calcium and potassium salts and amino group of pharmaceutically acceptable salts include hydrobromide, sulfate, hydrogen sulfate, phosphate, hydrogen phosphate, dihydrogen phosphate, acetate, succinate, citrate, tartrate, lactate, mandelate, methane sulfonate (mesylate) and p-toluene sulfonate (tosylate). They may be prepared by manufacturing method or manufacturing process known in the art.

In addition, since pyridine carboxylic acid-based compound having structure of the General formula (I) have asymmetric center, pyridine carboxylic acid-based compound having structure of the General formula (I) may be present to enantiomer and all optical isomers and R or S stereoisomers and mixtures of pyridine carboxylic acid-based compound having structure of the General formula (I) included within the scope of the present invention. The present invention includes the use of racemate, at least one enantiomer, at least one diastereomer or mixtures of thereof, and isomer separation method or manufacturing process known in the art.

In one aspect of the present invention, there is provided a pyridine carboxylic acid-based compound represented by the General formula (I) having an antagonistic activity to P2X1 and P2X3 receptors, isomers or pharmaceutically acceptable salt thereof:

It is another object of this invention to provide a method for preparing compound represented by the General formula (I). It may be synthesized chemically by methods represented by Reaction schemes, but not limited to.

The Reaction schemes represent a step-by-step manufacturing method of the representative compounds of the present invention and several compounds of the present invention may be prepared by modification such as changing the reagents, solvent and reaction order used in the synthesis process of the Reaction schemes 1 to 3.

Some of the compounds of the present invention are synthesized by process of no included within the scope of the Reaction schemes and the detailed synthesis process of these compounds is described in each of example, respectively.

(Reaction scheme 1) Preparation of 5-(2-carboxyethyl)-3-hydroxy-2-methylisonicotinic acid

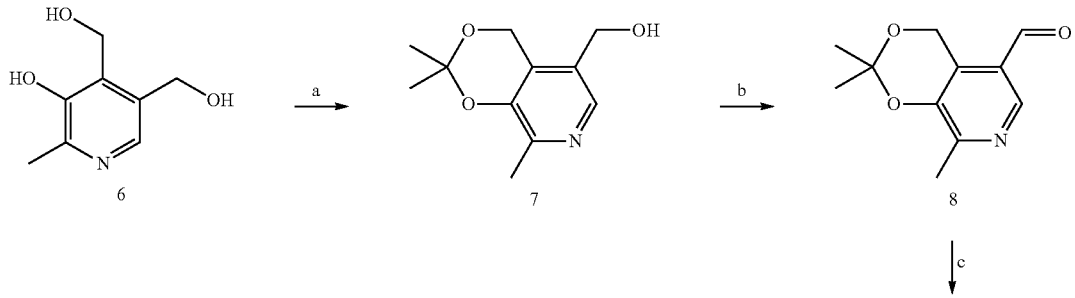

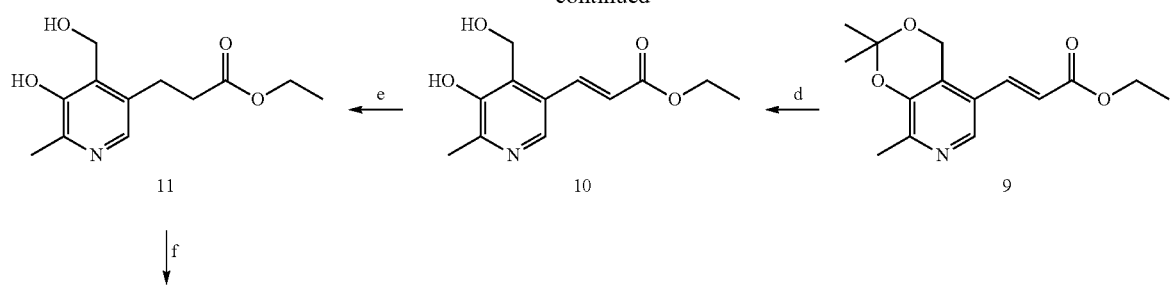

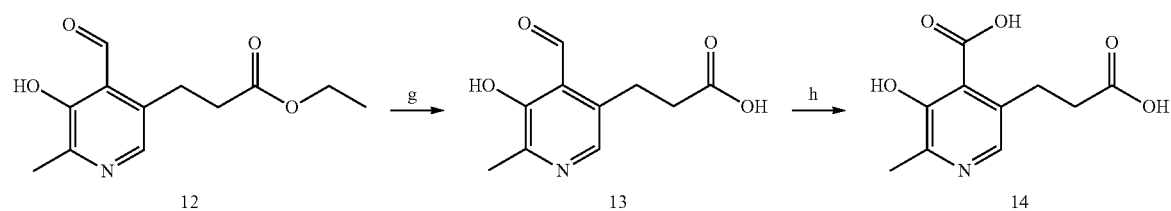

Reagents and conditions in wherein the Reaction scheme 1: (a) 2,2-dimethoxypropane, TsOH, acetone; (b) pyridinium dichromate, DCM; (c) triethylphosphoacetate, NaH, THF; (d) 10% formic acid in water, reflux, 3 hr; (e) Pd/C, H₂, MeOH; (f) MnO₂, DCM; (g) 5% KOH, MeOH; (h) OXONE, 0.2M DMF/ACN (Reaction scheme 2) Preparation of 5-(2-carboxyvinyl)-3-hydroxy-2-methylisonicotinic acid

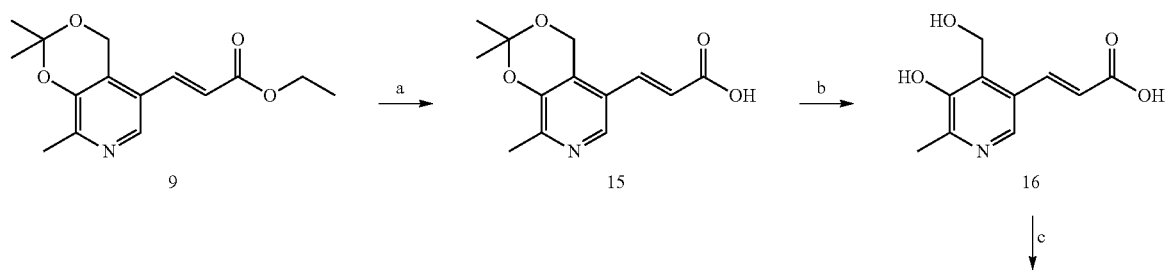

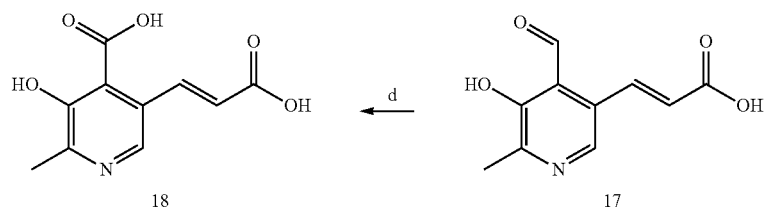

Reagents and conditions in wherein the Reaction scheme 2: (a) 5% KOH in MeOH, r.t, 3 hr; (b) 10% formic acid in water, reflux, 3 hr; (c) MnO₂, 0.3M THF/Water; (d) OXONE, 0.2M DMF/ACN (Reaction scheme 3) Preparation of 5-((benzyl(2-carboxyethyl)amino)methyl)-3-hydroxy-2-methylisonicotinic acid

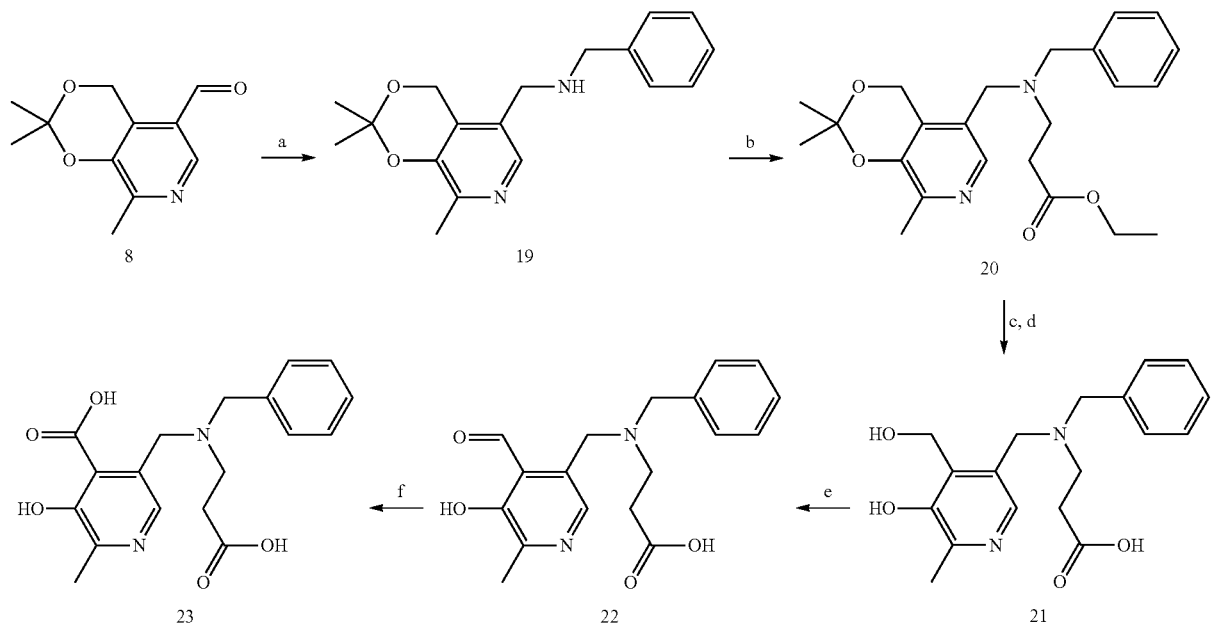

Reagents and conditions in wherein the Reaction scheme 3: (a) benzylamine, NaBH₃CN, 1% AcOH in DCM; (b) ethyl acrylate, EtOH, reflux, 24 hr; (c) 10% formic acid in water, reflux, 3 hr; (d) 5% KOH in MeOH, r.t, 3 hr; (e) MnO₂, 0.3M THF/Water; (f) OXONE, 0.2M DMF/ACN Wherein the Reaction scheme 1 represents manufacturing method of derivative of 5-(2-carboxyethyl)-3-hydroxy-2-methylisonicotinic acid; wherein the Reaction scheme 2 represents manufacturing method of derivative of 5-(2-carboxyvinyl)-3-hydroxy-2-methylisonicotinic acid; and wherein the Reaction scheme 3 represents manufacturing method of derivative of 5-((benzyl(2-carboxyethyl)amino)methyl)-3-hydroxy-2-methylisonicotinic acid, respectively and pyridoxal carboxylic acid derivatives or pyridoxic acid derivatives may be prepared by the reaction process such as disclosed wherein Reaction scheme 1 to 3.

For example, pyridoxine 6 is reacted with 2,2-dimethoxy propane in the presence of p-toluenesulfonic acid in acetone solvent and performed the oxidation reaction of 5-alcohol using pyridinium dichromate to prepare 5'-aldehyde derivative (8). The 5'-aldehyde derivative (8) is performed Wittig-Hornor reaction with triethylphosphoacetate to prepared the compound (9) and performed hydrolysis with weak acid such as 10% formic acid to prepared the compound (10). Under hydrogenation reaction conditions, α,β-unsaturated bond of the compound (10) is reduced and 4-hydroxymethyl group is converted to aldehyde group by manganese dioxide in methanol. The ester group of the compound (12) is hydrolyzed to convert its corresponding acid (13) and oxidized with OXONE to convert 4-carboxylic acid analogues.

α,β-unsaturated derivatives corresponding to the compounds 17 and 18, the compounds 13 and 14 may be prepared using the compound 9 as a starting material by the similar process to that mentioned above and the compound 23 may be synthesized by the 6-stage process disclosed in the reaction scheme 3.

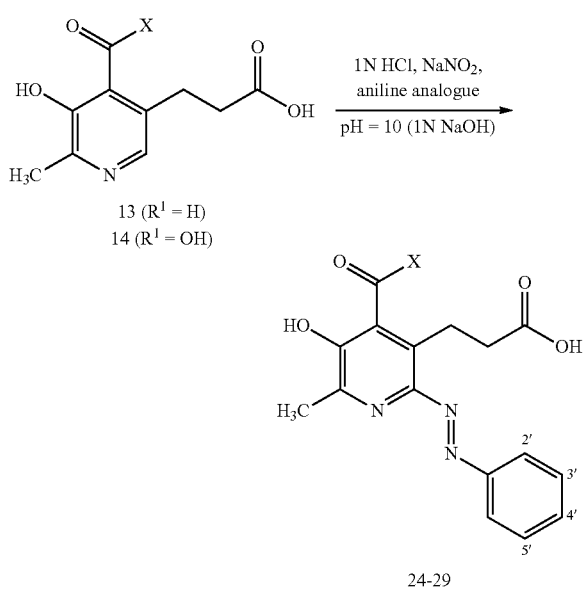

The reaction scheme 4 represents the general synthesis method of PPADS derivative through azo coupling reaction. For example, under the reductive amination condition in the presence of NaBH₃CN, aldehyde group of the compound (8) is reacted with benzyl amine to prepare resultant 19. Secondary amine group of the compound 19 is reacted with ethyl acrylate in ethanol by 1,4-addition reaction. Propane-2,2-dior protecting group is cut with weak acid such as 10% formic acid and successively hydrolyzed with base such as 5% KOH to prepare the compound (21). The resultant reacts with manganese dioxide in 0.3 M THF to prepare the compound (22). Aldehyde group of the compound (22) is converted to its corresponding carboxylic acid by OXONE. Finally, 4'-carboxylate, 4'-sulfonate and 2',5'-disulfonate derivative are prepared through azo coupling reaction in phenyl ring of compounds 24-29 (See Reaction scheme 4).

(Reaction scheme 5)
Synthesis method of 3,4-dicarboxypyridine derivatives

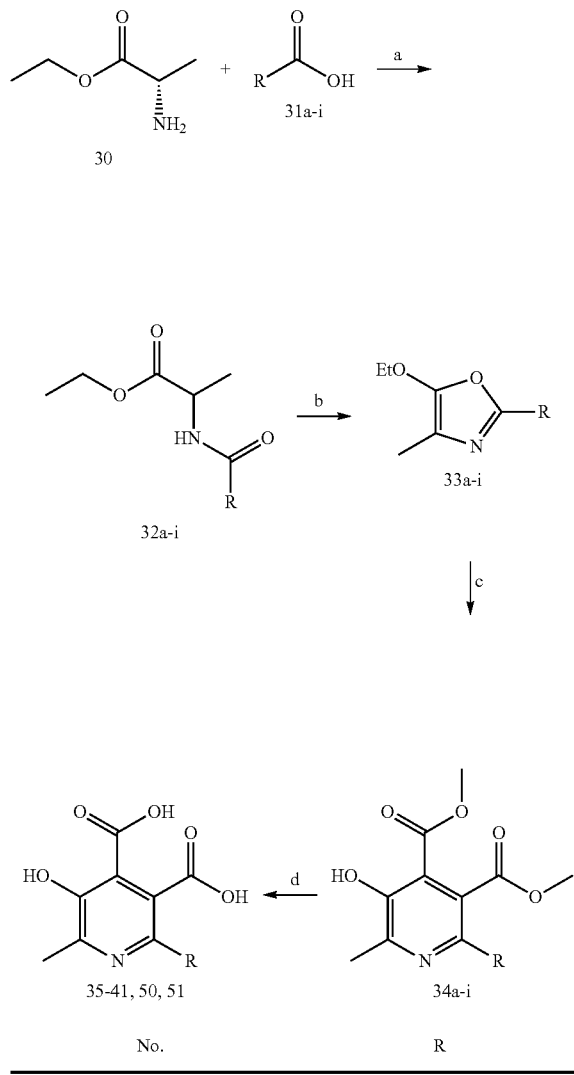

| No. | R |
|---|---|
| 35, a | $CH_2C_8H_8$ |
| 36, b | $CH_2CH_2C_6H_6$ |
| 37, c | $CH_2CH_2C_8H_6$-4-$OCH_3$ |
| 38, d | $CH=CHC_6H_6$ |
| 39, e | $CH_2CH_2C_6H_6$-4-$COOCH_3$ |
| 40, f | $CH_2CH_2C_6H_6$-3-$OCH_3$ |
| 41, g | $CH_2CH_2C_8H_6$-2-$OCH_3$ |
| 50, h | $CH_2CH(C_6H_6)_2$ |
| 51, i | $CH_2C_{10}H_7$ |

Reagents and conditions in the reaction scheme 5: (a) TEA, EDCI, DCM, room temperature, 2 hr (b) $P_2O_5$, $CHCl_3$, 2 hr, (c) dimethyl maleate, neat, 5 hr (d) 20% KOH (aq).

(Reaction scheme 6)
Synthesis method of 4-acetyl-3-dicarboxypyridine derivatives

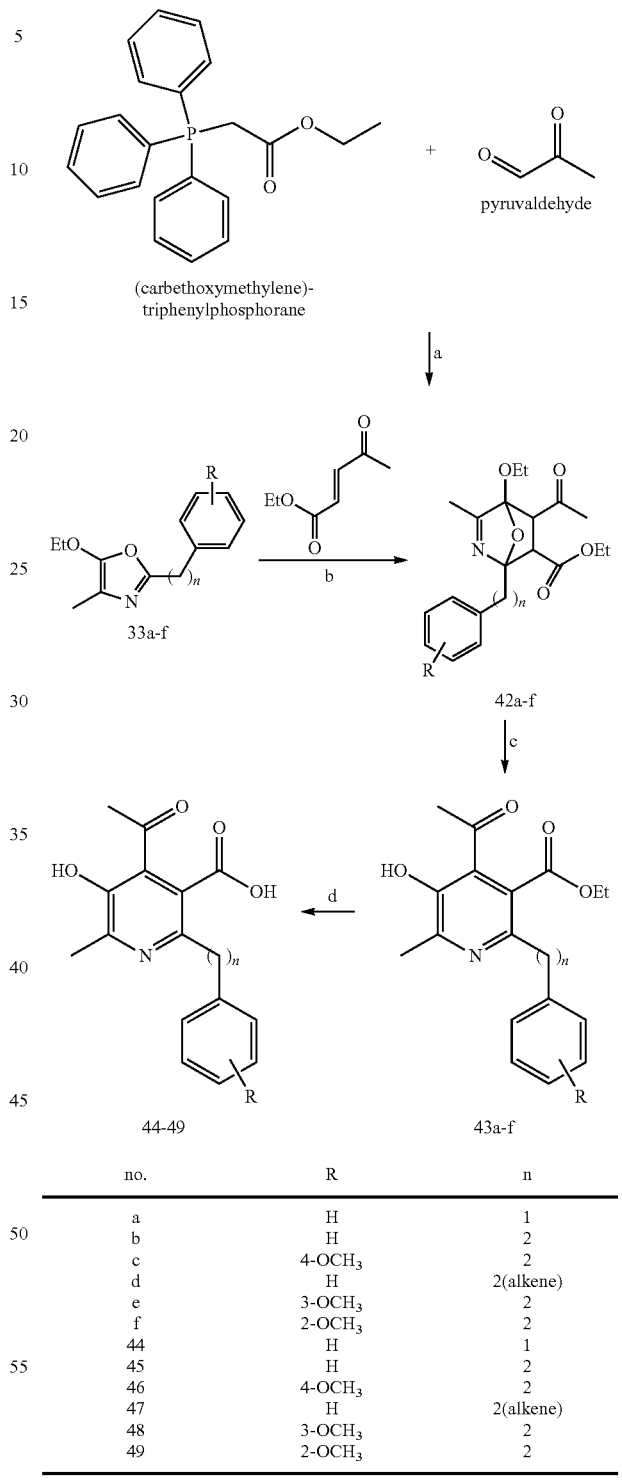

| no. | R | n |
|---|---|---|
| a | H | 1 |
| b | H | 2 |
| c | 4-$OCH_3$ | 2 |
| d | H | 2(alkene) |
| e | 3-$OCH_3$ | 2 |
| f | 2-$OCH_3$ | 2 |
| 44 | H | 1 |
| 45 | H | 2 |
| 46 | 4-$OCH_3$ | 2 |
| 47 | H | 2(alkene) |
| 48 | 3-$OCH_3$ | 2 |
| 49 | 2-$OCH_3$ | 2 |

Reagents and conditions in the Reaction scheme 6: (a) DMF, DCM, at room temperature, 24 hr (b) (E)-ethyl 4-oxopent-2-enoate, neat, 5 hr (c) HCl(g), EtOH, 0° C., (e) 5% KOH in MeOH, at room temperature.

The reaction schemes 5 and 6 represent the synthesis method of 3,4-dicarboxypyridine derivatives and 4-acetyl-3-dicarboxypyridine derivatives, respectively.

For example, 3,4-dicarboxypyridine derivative compounds 35-41 and 4-acetyl-3-dicarboxypyridine derivative compounds 44-49 may be synthesized by L-alanine ethyl ester as starting material using synthesis process disclosed in Reaction scheme 5 and 6.

In the presence of EDCI coupling agent, L-alanine ethyl ester (30) is combined with suitable carboxylic acid derivatives 31a-g to prepare compounds 32a-g. The ring cleavage reaction of the compounds 32a-g using phosphorus pentoxide is capable of inducing favorable reactions to oxazole compounds 33a-g with about 92% yield by the 3-stage process. Under refluxing conditions, pyridine ring synthesis is achieved using dimethyl maleate through Diels-Alder reaction of the compounds 33a-g. Finally, compounds 34a-g are treated with base such as 20% KOH to prepare final target substance 35-41 (see the Reaction scheme 5). For introducing acetyl group at pyridine ring 4-site of compounds 34a-g, pyridine derivative compounds 44-49 may be prepared by Diels-Alder reaction with (E)-ethyl 4-oxopent-2-enoate (see the Reaction scheme 6).

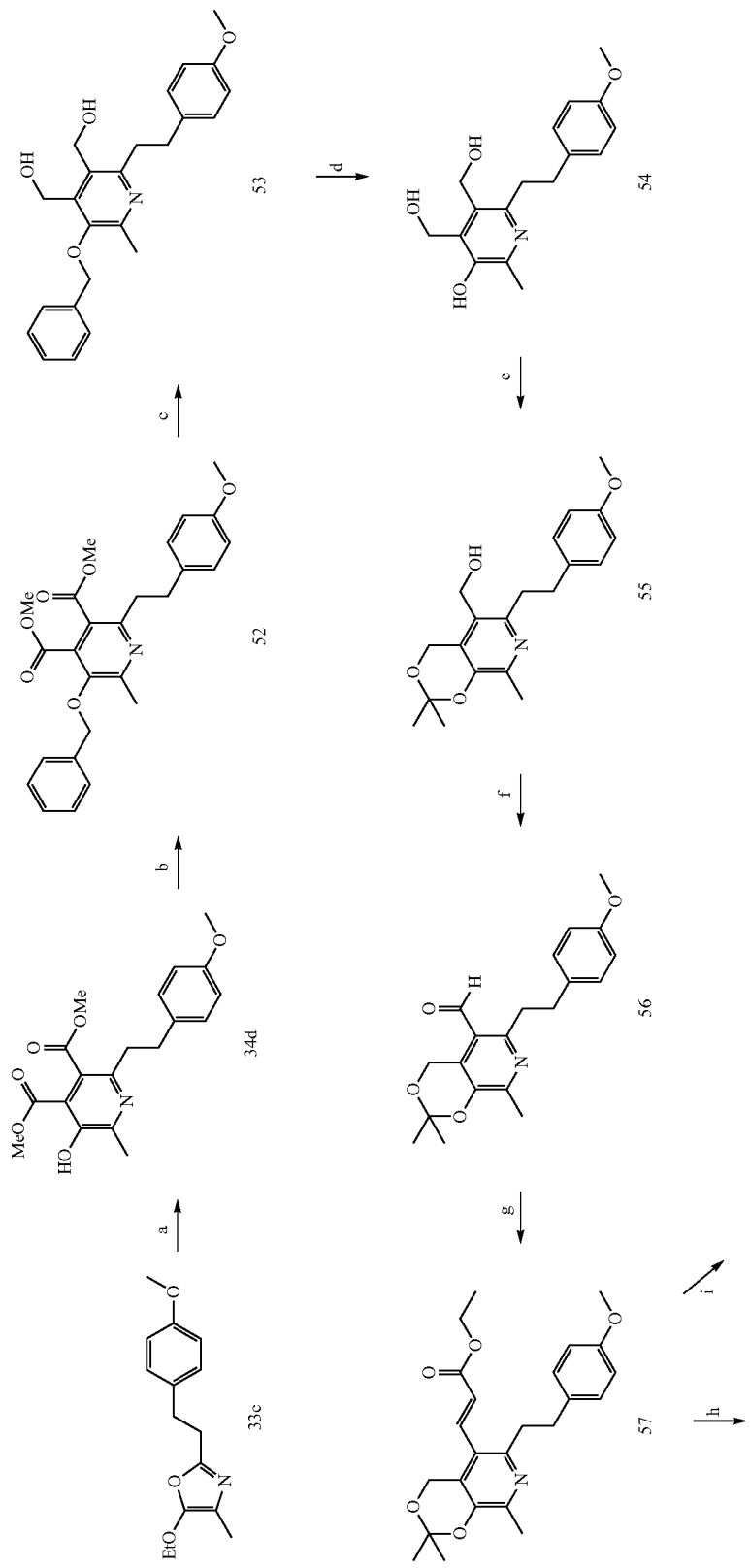
(Reaction scheme 6) Synthesis method of 4-formyl-3-carboxypyridine derivatives

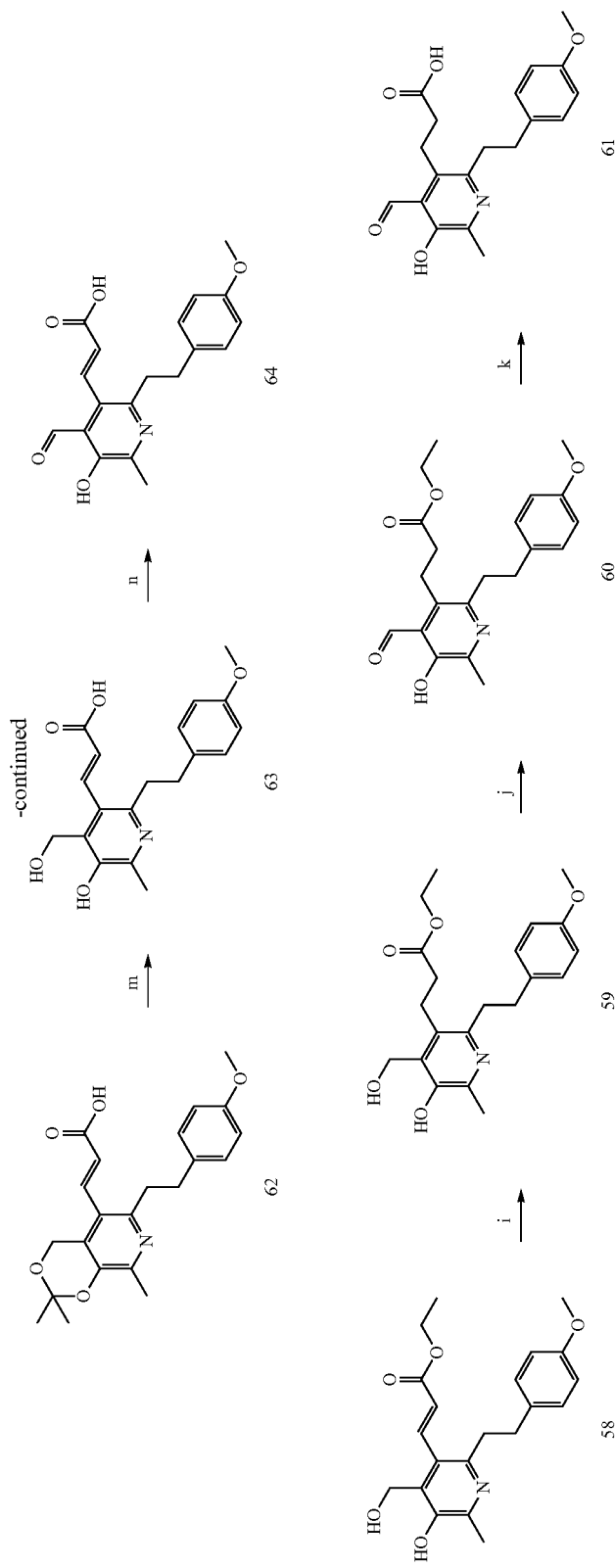
Reagents and conditions in wherein the Reaction scheme 6: (a) Dimethyl maleate, Et—OH, HCl gas; (b) benzyl bromide, Acetone, K₂CO₃; (c) LiAlH₄, THF; (d,i) Pd/C, H₂ gas, MeOH; (e) 2,2-dimethoxypropane, p-TsOH, acetone; (f) pyridinium dichromate, DCM; (g) triethylphoshpoacetate, NaH, THF; (h,m,p) 10% formic acid, reflux; (j,n,q) MnO₂, DCM; (k,l) 5% KOH in MeOH; (o) oxone, 2M DMF/ACN.

The Reaction scheme 7 represents synthesis method of 4-formyl-3-carboxypyridine derivatives.

For example, 4-formyl-3-carboxypyridine derivative compounds 61 and 64 may be synthesized by oxazole compound 33d as starting material using synthesis process disclosed in Reaction scheme 7. Under refluxing conditions, pyridine ring synthesis is achieved with dimethyl maleate through Diels-Alder reaction of compounds 33d. Finally, after coupling reaction with benzylbromide, the compounds 34d is reduced by reductant such as lithium aluminum hydride and removed benzyl part to prepare the compound 54 under hydrogenation reaction condition. The compound 54 is reacted with 2,2-dimethoxy-propane in the presence of p-toluenesulfonic acid in acetone solvent and performed the oxidation reaction of 5-alcohol using pyridinium dichromate in dichloromethane to prepare 5'-aldehyde derivative (56).

The protecting group 5'-aldehyde derivative (56) is performed Wittig-Hornor reaction with triethylphosphoacetate to prepare the compound (57) and performed hydrolysis with 10% formic acid to prepared the compound (58). Under hydrogenation reaction condition, α,β-unsaturated bond of the compound (58) is reducted and 4-hydroxymethyl group is converted to aldehyde group by manganese dioxide in methanol. The ester group of the compound (60) is hydrolyzed and converted to its corresponding acid to prepare final compound (61). The other final compound (63), α,β-unsaturated derivative corresponding to the compound 60 may be prepared using the compound 57 as a starting material by the similar process to that mentioned above. Also, final compound (67) may be prepared using the compound 56 as a starting material by the similar process to that mentioned above.

Therefore, the present invention is provided method for preparing pyridine carboxylic acid-based compound having structure of the General formula (I).

The General formula (I) compounds obtained from the preparation method represents powerful an antagonistic activity to $P2X_1$ and $P2X_3$ receptors, hence can be used as a drug for treating or preventing diseases caused by $P2X_1$ and $P2X_3$ receptor activity. The diseases are chronic inflammatory disease including degenerative arthritis, rheumatoid arthritis, asthma, chronic obstructive pulmonary disease or cystitis; neurological pain disease including neuropathic pain, allodynia, diabetic neuropathy, spontaneous pain, irritability pain, phantom limb pain or complex regional pain syndrome; or platelet aggregation-associated disease including arteriosclerosis, stroke, thrombosis, embolism, myocardial infarction, atherosclerosis, or peripheral blood circulatory disturbance.

Therefore, the present invention is provided a pharmaceutical composition for preventing or treating chronic inflammatory disease, neurological pain disease or platelet aggregation-associated disease caused by $P2X_1$ and $P2X_3$ receptor activity, comprising the compound represented by General formula (I) as an active ingredient.

As used herein, the term "chronic inflammatory disease caused by $P2X_1$ and $P2X_3$ receptor activity" encompasses degenerative arthritis, rheumatoid arthritis, asthma, chronic obstructive pulmonary disease or cystitis, the term "neurological pain disease caused by $P2X_1$ and $P2X_3$ receptor activity" encompasses neuropathic pain, allodynia, diabetic neuropathy, spontaneous pain, irritability pain, phantom limb pain or complex regional pain syndrome and the term "platelet aggregation-associated disease caused by $P2X_1$ and $P2X_3$ receptor activity" encompasses arteriosclerosis, stroke, thrombosis, embolism, myocardial infarction, atherosclerosis, or peripheral blood circulatory disturbance.

Therefore, the present invention is provided a $P2X_1$ and $P2X_3$ receptor antagonist, comprising the pyridine carboxylic acid-based compound represented by the General formula (I) as an active ingredient.

The present inventors have prepared novel pyridine carboxylic acid-based compounds and elucidated their powerful antagonistic activity to $P2X_1$ and $P2X_3$ receptors using two-electrode voltage clamp (TEVC) assay in Xenopus oocyte expressing mouse $P2X_1$ receptor and human $P2X_3$ receptor. As results, the present inventors have revealed that the present compounds have higher applicability as drugs for treating or preventing chronic inflammatory diseases or neuropathic pain diseases caused by $P2X_1$ and $P2X_3$ receptor activity.

In still another aspect of the present invention, the present invention relates to pharmaceutical composition for preventing or treating disease caused by $P2X_1$ and $P2X_3$ receptor activity, comprising pyridine carboxylic acid-based compound and method for treating above-mentioned disease using pyridine carboxylic acid-based compound.

As used herein, the term "preventing" or "prevention" refers to all action for inhibiting or delaying onset of disease caused by $P2X_1$ and $P2X_3$ receptor activity with administration of composition comprising pyridine carboxylic acid-based compound and the term "treating" or "treatment" refers to all action for ameliorating or changing better disease caused by $P2X_1$ and $P2X_3$ receptor activity with administration of composition comprising pyridine carboxylic acid-based compound.

Compositions and therapeutic methods of the present invention comprising pyridine carboxylic acid-based compound may be used for only human but also mammal such as cattle, horses, sheep, pigs, goat, camel, antelope, dog, cat which can occur disease caused by $P2X_1$ and $P2X_3$ receptor activity.

In addition, the present invention is provided a pharmaceutical composition for treating or preventing disease caused by $P2X_1$ and $P2X_3$ receptor activity, comprising the compound represented by General formula (I) as an active ingredient.

The composition comprising the compound of the present invention may further comprise acceptable carrier, excipient or diluent according to conventional methods commonly used.

The acceptable carrier, excipient or diluent included in the composition of the present disclosure includes lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methyl hydroxybenzoate, propylhydroxybenzoate, talc, magnesium stearate and mineral oil.

The composition comprising the compound of the present invention may be used in the form of preparations for oral administration such as powders, granules, tablets, capsules, suspensions, emulsions, syrups and aerosols, external application, suppositories or sterile injectable solution according to conventional methods commonly used.

More detailed, when the composition of the present disclosure is prepared as preparation, the composition of the present may be prepared using diluents such as fillers, extenders, binders, wetting agents, disintegrants and surfactants or excipients commonly used. Solid preparations for oral administration include tablets, pills, powders, granules, capsules, etc. These solid preparations may be prepared by mixing a compound with at least one excipients, for example, starch, calcium carbonate, sucrose, lactose, gelatin, etc. In addition to simple excipients, lubricants such as magnesium stearate and talc may be used. Liquid preparations for oral administration include suspensions, solutions, emulsions and syrups, etc. In addition to water commonly used as a simple diluent and liquid paraffin, various excipients, for example, wetting agents, sweetening agents, flavors, preservatives, etc. may be included. Preparations for parenteral administration include sterilized aqueous solutions, non-aqueous solvents, suspending agents, emulsions, freeze-drying agents, suppositories. Propylene glycol, polyethylene glycol, vegetable oils such as olive oil, injectable esters such as ethyl oleate may be used as non-aqueous solutions and suspending agents. Suppositories may include witepsol, macrogol, tween 61, cacao butter, laurin butter, glycerinated gelatin.

A preferable dose of the present invention depends on the conditions and body weight of the patient, the severity of the disease, drug forms, administration routes, and duration, but may be appropriately selected by those skilled in the art. However, preferably, a daily dosage of the compound of the present invention may be 0.001-100 mg/kg. The doses may be administered once or several times a day. An amount of the present invention may be preferably present in the ranges from 0.0001 to 10%, more preferably from 0.001 to 1% by weight based on a total weight of the composition.

Furthermore, the pharmaceutical composition of the present invention may be parenterally administered, and the parenteral administration may be effected by hypodermatic, intravenous or intramuscular injection. To prepare a parenteral formulation, a solution or suspension may be prepared by mixing the compound with a stabilizer or a buffer in water, and a unit dosage form such as an ampoule or a vial may be prepared.

The dosage form of the present compound includes a pharmaceutically acceptable salt form, single active ingredient, or combination with other pharmaceutically active compounds.

The pharmaceutical composition of the present invention may be administered in various administration routes. All administration manner may be expected and it may be administered by injection with oral, rectal, or intravenous, intramuscular, subcutaneous, intrauterine subdural or intracerebroventricular.

In still another aspect of the present invention, the present invention is provided a method for preventing or treating chronic inflammatory disease, neurological pain disease or platelet aggregation-associated disease caused by $P2X_1$ and $P2X_3$ receptor activity.

According to a preferred embodiment, the chronic inflammatory disease is degenerative arthritis, rheumatoid arthritis, asthma, chronic obstructive pulmonary disease or cystitis; the neurological pain disease is neuropathic pain, allodynia, diabetic neuropathy, spontaneous pain, irritability pain, phantom limb pain or complex regional pain syndrome; and the platelet aggregation-associated disease is arteriosclerosis, stroke, thrombosis, embolism, myocardial infarction, atherosclerosis, or peripheral blood circulatory disturbance.

The features and advantages of the present invention will be summarized as follows:

Provided are a novel pyridine carboxylic acid based compound used as a $P2X_1$ and $P2X_3$ receptor antagonist, a production method for the same and a composition comprising the same. The compound according to the present invention is a powerful antagonist of $P2X_1$ and $P2X_3$ receptors, and hence can be used as a drug for treating or preventing diseases involving neurological pain or chronic inflammatory diseases which are diseases caused by $P2X_1$ and $P2X_3$ receptor activity.

The present invention will now be described in further detail by examples. It would be obvious to those skilled in the art that these examples are intended to be more concretely illustrative and the scope of the present invention as set forth in the appended claims is not limited to or by the examples.

EXAMPLES

Materials and Methods 1-1. Reagents and Materials

ATP (disodium salt), pyridoxine and azo coupling reaction reagents were purchased from Aldrich (St. Louis, Mo.) and TCI (Tokyo). Aniline-2,5-disulfonic acid was purchased from K & K Laboratories, Inc. (Hollywood, Calif.). Other reagents and solvents were purchased from Merck (Darmstadt, Germany). Agonists and antagonists were manufactured from prepared stock solution (10 mM, stored frozen) in the extracellular bath solution.

1-2. Analysis Methods

Analytical TLC (thin-layer chromatography) was carried out on precoated silica glass plates (Merck silica gel 60, F254), and then visualized with UV rays (light) or stained with the sulfonic acid staining reagents. Flash column chromatography was performed on silica (Merck, 70-230 mesh). Proton nuclear magnetic resonance spectroscopy was measured with JEOL JNM-LA 300WB spectrometer and spectra were obtained in DMSO-$d_6$. Unless otherwise noted, chemical shifts are expressed as ppm downfield from tetramethylsilane or relative ppm from DMSO (2.5 ppm). Data are reported as follows: chemical shift, multiplicity (s, singlet; d, doublet; t, triplet; m, multiplet; b, broad; app., apparent), coupling constants and integration. Mass spectroscopy was carried out on MALDI-TOF and FAB instruments.

The determination of purity was performed on a Shimadzu SCL-10A VP HPLC system using Shimadzu Shimpack C18 analytical column (250 mm 4.6 mm, 5 μM, 100 Å) in linear gradient solvent systems. One solvent system (A) was 0.1 M triethylammonium acetate buffer: $CH3CN=95:5$ to 40:60 in 30 min with flow rate=1 mL/min. The other (B) was 5 mM tetrabutylammonium phosphate buffer: $CH_3CN=80:20$ to 40:60 in 30 min with flow rate=1 mL/min.

The cRNA of human $P2X_3$ receptor was obtained by reverse transcription of cDNA of human $P2X_3$ receptor, which was provided from German Max-Plank Institute laboratory (Dr. W. Stuhmer and Dr. F. Soto). The EST clones containing full-length cDNAs of mouse $P2X_1$ (clone ID: 4189541) and human $P2X_7$ receptor (clone ID: 5286944) were purchased from Invitrogen (CA, USA) and their sequences were confirmed by DNA sequencing.

1-3. Abbreviation

The definition of abbreviation used in this Example are:
ATP; adenosine 5'-triphosphate
BzATP3'-O-(4-benzoyl); benzoyl adenosine 5'-triphosphate
DMEM; Dulbecco's Modified Eagle Medium
EDAC; 1-ethyl-3-(3-dimethlyaminopropyl)carbodiimide
EDTA; ethylenediaminetetraacetic acid
HEK; human embryonic kidney
HEPES; N-(2-hydroxyethyl)piperazine-N'-(4-butanesulfonic acid)
HPLC; high-pressure liquid chromatography
iso-PPADS; pyridoxal-phosphate-6-azophenyl-2',5'-disulfonic acid
KN62; 1-[N,O-bis(1,5-isoquinolinesulphonyl)-N-methyl-L-tyrosyl]-4-henylpiperizine
NMPN; methyl-2-pyrrolidinone
PPADS; pyridoxalphosphate-6-azophenyl-2',4'-disulphonic acid
PyBOP; (Benzotriazol-1-yloxy)tripyrrolidinophosphonium Hexafluorophosphate
SAR; structure-activity relationship
SPPS; solid phase peptide synthesis
TFA; trifluoroacetic acid Example 1

Preparation of 3-(4-formyl-5-hydroxy-6-methylpyridin-3-yl) propanoic acid (13)

1-1. Preparation of ethyl 4-oxopent-2-enoate intermediate 46.7 mL of aqueous pyruvaldehyde (305.0 mmol) was dropwisely and slowly added at room temperature to 21.3 g of (carbethoxymethylene) triphenylphosphorane solution (61.0 mmol) in a small amount of dichloromethane solvent. The mixture was diluted using 30 mL of N,N-dimethylformamide, and stirred until the reaction was completed which was confirmed on TLC. The resultant was added with 300 ml of water and extracted with 700 mL of dichloromethane. The organic extract was washed successively with water and brine, dried with $MgSO_4$, and evaporated under reduced pressure to obtain, yielding the substance of interest in oil phase which was confirmed to consist of two isomers (E and Z isomers; 9:1) on $^1H$ NMR spectroscopy. From the mixture, E isomer of ethyl 4-oxopent-2-enoate ($R_f$ 0.80: hexanes-ethyl acetate=1:1) was isolated by flash column chromatography (elution solvent: n-hexanes-ethyl acetate=3:1). The isolated E isomer was verified by J coupling constant of NMR (E isomer J coupling constant=12~18 Hz).

$^1H$ NMR (acetone-$d_6$): 1.4 (3H, t, J=7.2 Hz, $CH_3$), 2.3 (3H, s, $COCH_3$), 4.15 (2H, q, J=7.2 Hz, $CH_2$), 6.6 (1H, d, J=15.0 Hz, =CH), 6.9 (1H, d, J=15.0 Hz, =CH); Z isomer: $R_f$ 0.74 (hexane-ethyl acetate=1:1); δ(acetone-$d_6$) 1.3 (3H, t, J=7.2 Hz, $CH_3$), 2.3 (3H, s, $COCH_3$), 4.15 (2H, q, J=7.2 Hz, $CH_2$), 5.9 (1H, d, J=12.0 Hz, =CH), 6.4 (1H, d, J=12.0 Hz, =CH).

1-2. Preparation of 2,2,8-Trimethyl-4H-[1,3]dioxino [4,5-d]pyridin-5-yl)methanol (7) intermediate 90 g (0.4 mol) of para-toluene sulfonic acid was added to the mixture of 20 g (0.1 mol) of pyridoxine and 244 mL (1.9 mol) of 2,2-dimethoxy-propane in flame-dried 3-necked round flask (1 L). The mixture was allowed to stir for 30 min at room temperature, neutralized with $NaHCO_3$ and concentrated under reduced pressure. After extraction with dichloromethane, the combinated organic layer was washed with water, dried with $MgSO_4$, filtrated, concentrated, followed by purifying column chromatography (solvent: dichloromethane/methanol=20:1) to obtain 2,2,8-Trimethyl-4H-[1,3]dioxino[4,5-c]pyridin-5-yl)methanol (7) as the target substance (yield: 65.7%).

$^1H$ NMR ($CDCl_3$): δ 1.52 (6H, s, 2×$CH_3$), 2.34 (3H, s, $CH_3$), 4.52 (2H, s, $CH_2$), 4.91 (2H, s, $CH_2$), 7.78 (1H, s, H-6);

MS (ESI): m/z=210.2 ($M^+$+1).

1-3. Preparation of 2,2,8-Trimethyl-4H-[1,3]dioxino [4,5-c]pyridine-5-carbaldehyde) (8) intermediate Pyridinium dihromate was added to stirred solution (23.9 mmol) of 5 g of 2,2,8-Trimethyl-4H-[1,3]dioxino[4,5-c] pyridin-5-yl)methanol (7) in 50 mL of anhydrous dichloromethane under vigorous stirring. After overnight incubation, the mixture was filtrated by methanol through celatum bed. The filtrate was evaporated under vacuum and purified by column chromatography (developing solvent: n-hexanes/ethyl acetate=3:1) to obtain solid form of 2,2,8-Trimethyl-4H-[1,3]dioxino[4,5-c]pyridine-5-carbaldehyde) (8) as the target substance (yield: 67.5%).

$^1H$ NMR ($CDCl_3$) δ 1.57 (6H, s, 2×$CH_3$), 2.51 (3H, s, $CH_3$), 5.18 (2H, s, $CH_3$), 8.48 (1H, s, H-6), 10.05 (1H, s, CHO);

MS (ESI): m/z=208.0 ($M^+$+1).

1-4. Preparation of Ethyl 3-(2,2,8-trimethyl-4H-[1, 3]dioxino[4,5-c]pyridin-5-yl)acrylate (9) intermediate 13 mL (16.8 mmol) of triethyl phosphonium acetate was dropwisely added to 500 mg of NaH suspension (16.9 mmol) in anhydrous tetrahydrofuran. The color of mixture turned clearly yellow with be emitted hydrogen gas. After 5 min stirring, 3.2 g of tetrahydrofuran (2,2,8-Trimethyl-4H-[1,3]dioxino[4,5-c]pyridine-5-carbaldehyde) (8) (15.3 mmol) was added to the reaction solution and stirred for 1 hr. The mixture was extracted with chloroform and brine. The organic residue was combinated, dried with $MgSO_4$, filtrated, followed by concentration and purifying with column chromatography (developing solvent: n-hexanes/ethyl acetate=3:1) to obtain solid form of Ethyl 3-(2,2,8-trimethyl-4H-[1,3]dioxino[4,5-c]pyridin-5-yl)acrylate (9) as the target substance (yield: 81.3%).

$^1H$ NMR ($CDCl_3$) δ 1.33 (3H, s, $CH_3$), 1.57 (6H, s, 2×$CH_3$), 2.44 (3H, s, $CH_3$), 4.28 (2H, q, J=8.8 Hz, $CH_2$), 4.93 (2H, s, $CH_2$), 6.37 (1H, d, J=16.6 Hz, CH), 7.54 (1H, d, J=16.6 Hz, CH), 8.26 (1H, s, H-6);

MS (ESI): m/z=278.3 ($M^+$+1).

1-5. Preparation of Ethyl 3-(5-hydroxy-4-(hydroxymethyl)-6-methylpyridin-3-yl)acrylate (10) intermediate 3 g of Ethyl 3-(2,2,8-trimethyl-4H-[1,3]dioxino[4,5-c] pyridin-5-yl)acrylate (9) solution (10.8 mmol) in 20 mL 10% formic acid solution was refluxed for 3 hrs. After cooling at room temperature, the mixture was extracted with chloroform and saturated $NaHCO_3$. The organic extract was combinated, dried with $MgSO_4$, filtrated, followed by concentration and purifying with column chromatography (developing solvent: dichloromethane/methanol=10:1) to obtain solid form of Ethyl 3-(5-hydroxy-4-(hydroxymethyl)-6-methylpyridin-3-yl)acrylate (10) as the target substance (yield: 97.8%).

$^1H$ NMR ($CDCl_3$) δ 1.35 (3H, s, $CH_3$), 2.48 (3H, s, $CH_3$), 4.28 (2H, q, J=8.8 Hz, $CH_2$), 5.12 (2H, s, $CH_2$), 6.30 (1H, d, J=16.6 Hz, CH), 7.67 (1H, d, J=16.6 Hz, CH), 8.14 (1H, s, H-6);

MS (ESI): m/z=238.1 ($M^+$+1).

1-6. Preparation of Ethyl 3-(5-hydroxy-4-(hydroxymethyl)-6-methylpyridin-3-yl)propanoate (11) intermediate 0.5 g of Pd/C was added to 2 g of Ethyl 3-(5-hydroxy-4-(hydroxymethyl)-6-methylpyridin-3-yl)acrylate (10) (8.4 mmol) in dichloromethane, to which was stirred for 4 hrs under hydrogen atmosphere. The mixture was filtrated through celatum bed. The filtrate was evaporated under reduced pressure and purified by column chromatography (developing solvent: chloroform/methanol=10:1) to obtain solid form of Ethyl 3-(5-hydroxy-4-(hydroxymethyl)-6-methylpyridin-3-yl)propanoate (11) as the target substance (yield: 89.2%).

$^1H$ NMR ($CDCl_3$) δ 1.23 (3H, t, J=7.1 Hz, $CH_3$), 2.40 (3H, s, $CH_3$), 2.50 (2H, t, J=7.6 Hz, $CH_2$), 2.80 (2H, t, J=7.6 Hz, $CH_2$), 4.10 (2H, q, J=7.1 Hz, $CH_2$), 4.99 (2H, s, $CH_2$), 7.73 (1H, s, H-6);

MS (ESI): m/z=240.1 ($M^+$+1).

1-7. Preparation of Ethyl 3-(4-formyl-5-hydroxy-6-methylpyridin-3-yl)propanoate (12) intermediate Activated manganese dioxide was added to 1 g (4.2 mmol) of Ethyl 3-(5-hydroxy-4-(hydroxymethyl)-6-methylpyridin-3-yl)propanoate (11) in 50 mL of anhydrous dichloromethane with stirring vigorously for 2 hrs under nitrogen atmosphere at room temperature. The mixture was filtrated through celatum bed, evaporated under reduced pressure and purified by column chromatography (developing solvent: n-hexanes/ethyl acetate=4:1) to obtain solid form of Ethyl 3-(4-formyl-5-hydroxy-6-methylpyridin-3-yl)propanoate (12) as the target substance (yield: 71.1%).

¹H NMR (CDCl₃) δ 1.24 (3H, t, J=7.1 Hz, CH₃), 2.51 (3H, s, CH₃), 2.69 (2H, t, J=7.6 Hz, CH₂), 3.25 (2H, t, J=7.6 Hz, CH₂), 4.12 (2H, q, J=7.1 Hz, CH₂), 8.02 (1H, s, H-6), 10.46 (1H, s, CHO);
MS (ESI): m/z=238.1 (M⁺+1).

1-8. Preparation of Ethyl 3-(4-Formyl-5-hydroxy-6-methylpyridin-3-yl)propanoic acid (13) intermediate 330 mg of Ethyl 3-(4-formyl-5-hydroxy-6-methylpyridin-3-yl)propanoate (12) (1.4 mmol) was added to 5% KOH in methanol with stirring vigorously for 1 hr. The reaction solvent was removed by evaporation and subject to ion-exchange resin column chromatography (Amberlite CG-50 resin) to obtain solid form of Ethyl 3-(4-Formyl-5-hydroxy-6-methylpyridin-3-yl)propanoic acid (13) as the target substance (yield: 53.9%).
¹H NMR (D₂O) δ 2.47 (3H, s, CH₃), 2.55 (2H, t, J=7.5 Hz, CH₂), 3.15 (2H, t, J=7.5 Hz, CH₂), 7.58 (1H, s, H-6), 10.44 (1H, s, CHO);
MS (ESI): m/z=210.2 (M⁺+1).

Example 2

Preparation of 5-(2-Carboxyethyl)-3-hydroxy-2-methyl isonicotinic acid (14)

520 mg (0.8 mmol) of oxone was added with agitating vigorously over 3 hr to 177 mg of Ethyl 3-(4-Formyl-5-hydroxy-6-methylpyridin-3-yl)propanoic acid (13) (0.8 mmol) in 0.2 M DMF solvent in acetonitrile. The color of reaction color turned colorless from yellow. The resultant was subject to ion-exchange resin column chromatography (Amberlite CG-50 resin) and freeze-dried to obtain solid form of 5-(2-Carboxyethyl)-3-hydroxy-2-methyl isonicotinic acid (14) as the target substance (yield: 47.7%).
¹H NMR (D₂O) δ 2.34 (3H, s, CH₃), 2.50 (2H, t, J=7.5 Hz, CH₂), 2.74 (2H, t, J=7.5 Hz, CH₂), 7.53 (1H, s, H-6);
MS (ESI): m/z=226.3 (M⁺+1).

Example 3

Preparation of 3-(2,2,8-Trimethyl-4H-[1,3]dioxino[4,5-c]pyridin-5-yl)acrylic acid (15)

3 g of Ethyl 3-(2,2,8-trimethyl-4H-[1,3]dioxino[4,5-c]pyridin-5-yl)acrylate (9) (12.1 mmol) was added to 50 mL of aqueous 5% KOH solution in 100 mL of methanol with stirring vigorously for 3 hrs. The resultant was concentrated under reduced pressure, subject to ion-exchange resin column chromatography (Amberlite CG-50 resin) and freeze-dried to obtain solid form of 3-(2,2,8-Trimethyl-4H-[1,3]dioxino[4,5-c]pyridin-5-yl)acrylic acid (15) as the target substance (yield: 74.5%).
¹H NMR (D₂O) δ 1.57 (6H, s, 2×CH₃), 2.38 (3H, s, CH₃), 5.08 (2H, s, CH₂), 6.43 (1H, d, J=16.6 Hz, CH), 7.20 (1H, d, J=16.6 Hz), 8.17 (1H, s, H-6);
MS (ESI): m/z=250.2 (M⁺+1).

Example 4

Preparation of (3-(5-Hydroxy-4-(hydroxymethyl)-6-methylpyridin-3-yl)acrylic acid (16)

2 g of 5-(2-Carboxyethyl)-3-hydroxy-2-methyl isonicotinic acid (14) (8.0 mmol) was added to 4 N aqueous HCl solution in methanol and stirred for 2 days. The reaction was searched by an analytic HPLC system and subject to ion-exchange resin column chromatography (Amberlite CG-50 resin) to obtain solid form of (3-(5-Hydroxy-4-(hydroxymethyl)-6-methylpyridin-3-yl)acrylic acid (16) as the target substance (yield: 60.5%).
¹H NMR (D₂O) δ 2.45 (3H, s, CH₃), 4.87 (2H, s, CH₂), 6.43 (1H, d, J=16.6 Hz, CH), 7.26 (1H, d, J=16.6 Hz, CH), 7.98 (1H, s, H-6);
MS (ESI): m/z=210.1 (M⁺+1).

Example 5

Preparation of 3-(4-Formyl-5-hydroxy-6-methyl-pyridin-3-yl)acrylic acid (17)

2 g of 5-(2-Carboxyethyl)-3-hydroxy-2-methyl isonicotinic acid (14) (8.0 mmol) was added to 4N aqueous HCl solution in methanol and stirred for 2 days. The reaction was searched by an analytic HPLC system and subject to ion-exchange resin column chromatography (Amberlite CG-50 resin) to obtain solid form of 3-(4-Formyl-5-hydroxy-6-methylpyridin-3-yl)acrylic acid (17) as the target substance (yield: 52.4%).
¹H NMR (DMSO-d₆) δ 2.39 (3H, s, CH₃), 6.95 (1H, d, CH, J=16.1 Hz), 7.58 (1H, d, CH, J=16.1 Hz), 8.34 (1H, s, H-6);
MS (ESI): m/z=208.2 (M⁺+1).

Example 6

Preparation of 5-(2-Carboxyvinyl)-3-hydroxy-2-methylisonicotinic acid (18)

2 g of 5-(2-Carboxyethyl)-3-hydroxy-2-methyl isonicotinic acid (14) (8.0 mmol) was added to 4N aqueous HCl solution in methanol and stirred for 2 days. The reaction was searched by an analytic HPLC system and subject to ion-exchange resin column chromatography (Amberlite CG-50 resin) to obtain solid form of 5-(2-Carboxyvinyl)-3-hydroxy-2-methylisonicotinic acid (18) as the target substance (yield: 71.3%).
¹H NMR (DMSO-d₆) δ 2.31 (3H, s, CH₃), 6.12 (1H, d, CH, J=16.8 Hz), 7.89 (1H, d, CH, J=16.8 Hz), 8.76 (1H, s, H-6);
MS (ESI): m/z=224.2 (M⁺+1).

Example 7

Preparation of N-Benzyl-1-(2,2,8-trimethyl-4H-[1,3]dioxino[4,5-c]pyridin-5-yl)methanamine (19)

126 μL (1.2 mmol) of benzyl amine was added to 200 mg of 2,2,8-Trimethyl-4H-[1,3]dioxino[4,5-c]pyridine-5-carbaldehyde (8) (1.0 mmol) solution dissolved in 1.0% acetic acid solution in dichloromethane and stirred for 30 min. The reaction mixture was added to 90 mg NaBH₃CN (1.4 mmol) and stirred for 4 hrs. The resultant was extracted with chloroform and saturated NaHCO₃, dried with MgSO₄, filtrated, concentrated, followed by purifying with column chromatography (developing solvent: dichloromethane/methanol=30:1) to obtain solid form of N-Benzyl-1-(2,2,8-trimethyl-4H-[1,3]dioxino[4,5-c]pyridin-5-yl)methanamine (19) as the target substance (yield: 50.7%).
¹H NMR (CDCl₃) δ 1.54 (6H, s, 2×CH₃), 2.39 (3H, s, CH₃), 3.64 (2H, s, CH₂), 3.78 (2H, s, CH₂), 4.93 (2H, s, CH₂), 7.25~7.40 (5H, m, phenyl), 7.92 (1H, s, H-6);

MS (ESI): m/z=299.4 (M⁺+1).

Example 8

Preparation of Ethyl 3-(benzyl((2,2,8-trimethyl-4H-[1,3]dioxino[4,5-c]pyridin-5-yl)methyl)amino)propanoate (20)

37 µL (0.3 mmol) of ethyl acetate was added to 50 mg of N-Benzyl-1-(2,2,8-trimethyl-4H-[1,3]dioxino[4,5-c]pyridin-5-yl)methanamine (19) solution (0.2 mmol) in ethanol was added and stirred overnight at room temperature. The mixture was concentrated under reduced pressure and purified by column chromatography (developing solvent: chloroform/methanol=50:1) to obtain solid form of Ethyl 3-(benzyl((2,2,8-trimethyl-4H-[1,3]dioxino[4,5-c]pyridin-5-yl)methyl)amino)propanoate (20) as the target substance (yield: 34.6%).

$^1$H NMR (CDCl$_3$) δ 1.14 (3H, t, J=7.2 Hz, CH$_3$), 1.45 (6H, s, 2×CH$_3$), 2.31 (3H, s, CH$_3$), 2.39 (2H, t, J=7.2 Hz, CH$_2$), 2.68 (2H, t, J=7.2 Hz, CH$_2$), 3.36 (2H, s, CH$_2$), 3.46 (2H, s, CH$_2$), 4.01 (2H, q, J=7.2 Hz, CH$_2$), 4.69 (2H, s, CH$_2$), 7.17~7.26 (5H, m, phenyl), 7.84 (1H, s, H-6);

MS (ESI): m/z=399.5 (M⁺+1).

Example 9

Preparation of 3-(Benzyl((5-hydroxy-4-(hydroxymethyl)-6-methylpyridin-3-yl)methyl)amino)propanoic acid (21)

2 g of 5-(2-Carboxyethyl)-3-hydroxy-2-methyl isonicotinic acid (14) (8.0 mmol) was added to 4N aqueous HCl solution in methanol and stirred for 2 days. The reaction was searched by an analytic HPLC system and subject to ion-exchange resin column chromatography (Amberlite CG-50 resin) to obtain solid form of 3-(Benzyl((5-hydroxy-4-(hydroxymethyl)-6-methylpyridin-3-yl)methyl)amino)propanoic acid (21) as the target substance (yield: 46.9%).

$^1$H NMR (D$_2$O) δ 2.42 (3H, s, CH$_3$), 2.53 (2H, t, J=7.2 Hz, CH$_2$), 3.02 (2H, t, J=7.2 Hz, CH$_2$), 3.95 (2H, s, CH$_2$), 4.62 (2H, s, CH$_2$), 7.35~7.45 (5H, m, phenyl), 7.62 (1H, s, H-6);

MS (ESI): m/z=331.4 (M⁺+1).

Example 10

Preparation of 3-(Benzyl((4-formyl-5-hydroxy-6-methylpyridin-3-yl)methyl)amino)propanoic acid (22)

2 g of 5-(2-Carboxyethyl)-3-hydroxy-2-methyl isonicotinic acid (14) (8.0 mmol) was added to 4N aqueous HCl solution in methanol and stirred for 2 days. The reaction was searched by an analytic HPLC system and subject to ion-exchange resin column chromatography (Amberlite CG-50 resin) to obtain solid form of 3-(Benzyl((4-formyl-5-hydroxy-6-methylpyridin-3-yl)methyl)amino)propanoic acid (22) as the target substance (yield: 34.5%).

$^1$H NMR (CDCl$_3$) δ 2.47 (3H, s, CH$_3$), 2.51 (2H, t, J=6.9 Hz, CH$_2$), 2.78 (2H, t, J=6.9 Hz, CH$_2$), 3.61 (2H, s, CH$_2$), 3.76 (2H, s, CH$_2$), 7.24~7.33 (5H, m, phenyl), 8.01 (1H, s, H-6), 10.21 (1H, s, CHO);

MS (ESI): m/z=329.4 (M⁺+1).

Example 11

Preparation of 5-((Benzyl(2-carboxyethyl)amino) methyl)-3-hydroxy-2-methylisonicotinic acid (23)

2 g of 5-(2-Carboxyethyl)-3-hydroxy-2-methyl isonicotinic acid (14) (8.0 mmol) was added to 4N aqueous HCl solution in methanol and stirred for 2 days. The reaction was searched by an analytic HPLC system and subject to ion-exchange resin column chromatography (Amberlite CG-50 resin) to obtain solid form of 5-((Benzyl(2-carboxyethyl)amino)methyl)-3-hydroxy-2-methylisonicotinic acid (23) as the target substance (yield: 42.6%).

$^1$H NMR (D$_2$O) δ 2.58 (3H, s, CH$_3$), 2.55 (2H, t, J=6.9 Hz, CH$_2$), 2.82 (2H, t, J=6.9 Hz, CH$_2$), 3.71 (2H, s, CH$_2$), 3.82 (2H, s, CH$_2$), 7.24~7.33 (5H, m, phenyl), 8.01 (1H, s, H-6);

MS (ESI): m/z=345.4 (M⁺+1).

Example 12

General Synthesis Process of Azo Group-Containing Compounds (Compound 24-29)

Stirred solution of aniline analogues (0.1 mmol) and 13 mg of Na$_2$CO$_3$ solution (0.1 mmol) in 1 mL H$_2$O was added to 8 mg (0.1 mmol) of NaNO$_2$ at 0° C. The resultant was dropwisely added to 60 µL (0.3 mmol) of 6 N HCl. The mixture was stirred for 5-10 min at 0° C. To the resultant, carboxylic acid analogues of pyridoxal or pyridoxic acid (0.1 mmol) in 1 mL of H$_2$O was added at a time and its pH was titrated by adding 1 N NaOH (~300 µL) to pH 10-11. The resultant color turned red from yellow (sometimes progressively) which means that the reaction occurs.

After stirring for 30 min at 0° C. and 30 min at 25° C., the mixture was purified by ion-exchange resin column chromatography (Amberlite CG-50 resin; H⁺ form, weak acid) using water as an elution solvent (flow rate amount: 0.5 mL/min). The red fraction representing a single peak on HPLC was collected and freeze-dried to obtain target substances having 95% purity or higher.

12-1. Preparation of 3-(2-((2,5-Disulfophenyl)diazenyl)-4-formyl-5-hydroxy-6-methylpyridin-3-yl) propanoic acid (24)

Solid form of 3-(2-((2,5-Disulfophenyl)diazenyl)-4-formyl-5-hydroxy-6-methylpyridin-3-yl)propanoic acid (24) was obtained by the similar manner to the method disclosed in Example 12 (yield: 28.5%).

$^1$H NMR (D$_2$O) δ 2.39 (3H, s, CH$_3$), 2.65 (2H, t, J=6.9 Hz, CH$_2$), 3.54 (2H, t, J=6.9 Hz, CH$_2$), 8.34 (1H, d, J=8.1 Hz, phenyl), 8.62 (1H, d, J=8.1 Hz, phenyl), 9.06 (1H, s, phenyl), 10.20 (1H, s, CHO);

MS (MALDI-TOF): m/z=474.4 (M⁺+1).

12-2. Preparation of 3-(2-Carboxyethyl)-2-((2,5-disulfophenyl)diazenyl)-5-hydroxy-6-methylisonicotinic acid (25)

Solid form of 3-(2-Carboxyethyl)-2-((2,5-disulfophenyl)diazenyl)-5-hydroxy-6-methylisonicotinic acid (25) was obtained by the similar manner to the method disclosed in Example 12 (yield: 32.4%).

$^1$H NMR (D$_2$O) δ 2.74 (3H, s, CH$_3$), 2.85 (2H, t, J=8.7 Hz, CH$_2$), 3.84 (2H, t, J=8.7 Hz, CH$_2$), 8.03 (1H, d, J=8.1 Hz, phenyl), 8.13 (1H, s, phenyl), 8.22 (1H, d, J=8.1 Hz, phenyl);

MS (MALDI-TOF): m/z=489.4 (M⁺+1).

12-3. Preparation of 3-(4-Formyl-5-hydroxy-6-methyl-2-((4-sulfophenyl)diazenyl)pyridin-3-yl) propanoic acid (26)

Solid form of 3-(4-Formyl-5-hydroxy-6-methyl-2-((4-sulfophenyl)diazenyl)pyridin-3-yl)propanoic acid (26) was obtained by the similar manner to the method disclosed in Example 12 (yield: 26.2%).

¹H NMR (D₂O) δ 2.43 (3H, s, CH₃), 2.65 (2H, t, J=6.9 Hz, CH₂), 3.50 (2H, t, J=6.9 Hz, CH₂), 7.67 (2H, d, J=8.4 Hz, phenyl), 7.82 (2H, d, J=8.4 Hz, phenyl), 10.29 (1H, s, CHO).
MS (MALDI-TOF): m/z=394.3 (M⁺+1).

12-4. Preparation of 3-(2-carboxyethyl)-5-hydroxy-6-methyl-2-((4-sulfophenyl)diazenyl)isonicotinic acid (27)

Solid form of 3-(2-carboxyethyl)-5-hydroxy-6-methyl-2-((4-sulfophenyl)diazenyl)isonicotinic acid (27) was obtained by the similar manner to the method disclosed in Example 12 (yield: 28.3%).
¹H NMR (D₂O) δ 2.65 (3H, s, CH₃), 2.73 (2H, t, J=7.2 Hz, CH₂), 3.68 (2H, t, J=7.2 Hz, CH₂), 7.79 (2H, d, J=7.2 Hz, phenyl), 7.98 (2H, d, J=7.2 Hz, phenyl);
MS (MALDI-TOF): m/z=410.3 (M⁺+1).

12-5. Preparation of 4-((3-(2-carboxyethyl)-4-formyl-5-hydroxy-6-methylpyridin-2-yl)diazenyl) benzoic acid (28)

Solid form of 4-((3-(2-carboxyethyl)-4-formyl-5-hydroxy-6-methylpyridin-2-yl)diazenyl)benzoic acid (28) was obtained by the similar manner to the method disclosed in Example 12 (yield: 32.5%).
¹H NMR (D₂O) δ 2.53 (3H, S, CH₃), 2.62 (2H, t, J=6.9 Hz, CH₂), 3.75 (2H, t, J=6.9 Hz, CH₂), 7.94 (2H, d, J=8.1 Hz, phenyl), 8.06 (2H, d, J=8.1 Hz, phenyl), 10.52 (1H, s, CHO).
MS (MALDI-TOF): m/z=358.3 (M⁺+1).

12-6. Preparation of 3-(2-carboxyethyl)-2-((4-carboxyphenyl)diazenyl)-5-hydroxy-6-methy lisonicotinic acid (29)

Solid form of 3-(2-carboxyethyl)-2-((4-carboxyphenyl)diazenyl)-5-hydroxy-6-methy lisonicotinic acid (29) was obtained by the similar manner to the method disclosed in Example 12 (yield: 24.5%).
¹H NMR (D₂O) δ 2.43 (3H, s, CH₃), 2.58 (2H, t, J=7.5 Hz, CH₂), 3.52 (2H, t, J=7.5 Hz, CH₂), 7.63 (2H, d, J=8.1 Hz, phenyl), 7.98 (2H, d, J=8.1 Hz, phenyl).
MS (MALDI-TOF): m/z=374.3 (M⁺+1).

Example 13

General Preparation Method of Dicarboxy Pyridine Derivatives (Compounds 35-41, 50 and 51)

13-1. Preparation of Amide Compound Intermediates (32a-i)

15 g (78.0 mmol) of EDCI [1-ethyl-3-(3-dimethylaminopropyl)carbodiimide] was introduced to various carboxylic acid compounds in 150 mL of dichloromethane, i.e., 2-phenylacetic acid (31a), 3-phenylpropanoic acid (31b), 3-(-4methoxyphenyl)propanoic acid (31c) cinnamic acid (31d), 3-((4methoxycarbonyl)phenyl)propanoic acid (31e), 3-(3-methoxyphenyl)propanoic acid (31f), 3-(2-methoxyphenyl)propanoic acid (31 g) 3,3-diphenylpropanoic acid (31 h), 2-naphtyl acetic acid (31i) (39.0 mol) and 6 g (39.0 mmol) of L-alanine ethyl ether solution, to which was dropwisely added triethylamine (39.0 mmol) for 30 min. The mixture was stirred for 12 hrs at room temperature. After reaction, the mixture was neutralized with Na₂CO₃ and extracted with water and dichloromethane. The organic layer was collected and treated with saturated Na₂SO₄. After filtration, the organic extract was concentrated under reduced pressure and subject to silica gel column chromatography (developing solvent: n-hexanes/ethyl acetate=1:1) to prepare intermediates as follows:

2-Phenylacetylamino-propionic acid ethyl ester (32a)

yield: 97.4%;
¹H-NMR (CDCl₃) δ 1.22 (3H, t, J=7.2 Hz, CH₃) 1.33 (3H, d, J=7.2 Hz, CH₃), 3.59 (2H, s, CH₂), 4.13 (2H, q, J=7.2 Hz, CH₂), 4.54 (1H, q, J=7.2 Hz, CH), 6.12 (1H, d, J=6.3 Hz, NH), 7.30 (2H, s, phenyl-1H), 7.32 (2H, s, phenyl-2H), 7.35 (1H, s, phenyl-3H);
MS (ESI): m/z=236.1 (M⁺+1).

2-(3-phenyl-propionylamino)-propionic acid ethyl ester (32b)

yield: 92.3%;
¹H-NMR (CDCl₃) δ 1.24 (3H, t, J=7.2 Hz, CH₃), 1.32 (3H, d, J=7.2 Hz, CH₃), 2.48 (2H, t, J=7.2 Hz, CH₂), 2.94 (2H, t, J=8.1 Hz, CH₂), 4.14 (2H, d, J=6.9 Hz, CH₂), 4.54 (1H, m, CH), 6.12 (1H, d, J=6.6 Hz, NH), 7.18 (1H, s, phenyl-1H), 7.20 (1H, s phenyl-2H), 7.21 (1H, s, phenyl-3H), 7.25 (1H, s, phenyl-4H), 7.28 (1H, s, phenyl-5H);
MS (MALDI-TOF): m/z=248.4 (M⁺+1).

(2-[3-(4-Methoxy-phenyl)-propionylamino]-propionic acid ethyl ester (32c)

yield: 95.6%;
¹H-NMR (CDCl₃) δ 1.25 (3H, t, J=7.2 Hz, CH₃), 1.33 (3H, d, J=6.9 Hz, CH₃), 2.48 (2H, t, J=5.1 Hz, CH₂), 2.89 (2H, t, J=7.5 Hz, CH₂), 3.78 (3H, s, CH₃O), 4.15 (2H, q, J=7.2 Hz, CH₂), 4.52 (1H, m, CH), 5.95 (1H, d, J=5.4 Hz, NH), 6.81 (2H, d, J=7.2 Hz, phenyl-1H), 7.10 (2H, d, J=9.0 Hz, phenyl-2H),
MS (MALDI-TOF): m/z=279.3 (M⁺+1).

2-(3-Phenyl-acroloylamino)-propionic acid ethyl ester (32d)

yield: 81.3%;
¹H-NMR (CDCl₃) δ 1.30 (3H, t, J=7.2 Hz, CH₃), 1.49 (3H, d, J=6.9 Hz, CH₃), 4.22 (2H, q, J=7.2 Hz, CH₂), 4.72 (1H, m, CH), 6.27 (1H, d, J=6.0 Hz, NH), 6.43 (1H, d, J=15.6 Hz, CH), 7.37 (3H, phenyl-1H), 7.51 (2H, phenyl-2H), 7.63 (1H, d, J=15.6 Hz, CH);
MS (ESI): m/z=248.2 (M⁺+1).

4-[2-(1-Ethoxycarbonyl-ethylcarbamoyl)-ethyl]-benzoic acid methyl ester) (32e)

yield: 81.3%;
¹H-NMR (CDCl₃) δ 1.25 (3H, t, J=7.2 Hz, CH₃), 1.33 (3H, d, J=6.9 Hz, CH₃), 2.48 (2H, t, J=5.1 Hz, CH₂), 2.89 (2H, t, J=7.5 Hz, CH₂), 3.78 (3H, s, CH₃O), 4.15 (2H, q, J=7.2 Hz, CH₂), 4.52 (1H, m, CH), 5.95 (1H, d, J=5.4 Hz, NH), 6.81 (2H, d, J=7.2 Hz, phenyl-1H), 7.10 (2H, d, J=9.0 Hz, phenyl-2H);
MS (ESI): m/z=307.5 (M⁺+1).

2-[3-(3-Methoxy-phenyl)-propionylamino]-propionic acid ethyl ester (32f)

yield: 67.2%;
¹H-NMR (CDCl₃) δ 1.22 (3H, t, J=7.2 Hz, CH₃), 1.35 (3H, d, J=7.2 Hz, CH₃), 2.51 (2H, t, J=6.9 Hz, CH₂), 2.93 (2H, t, J=8.1 Hz, CH₂), 3.80 (3H, s, CH₃O), 4.17 (2H, q, J=7.2 Hz, CH$_2$), 4.55 (1H, m, CH), 5.99 (1H, d, J=5.4 Hz, NH), 6.80 (2H, m, phenyl-1H), 7.22 (2H, m, phenyl-2H);
MS (ESI): m/z=280.3 (M$^+$+1).

Ethyl 2-(3-(2-methoxyphenyl)propanamido)propanoate (32 g)

yield: 79.8%;
$^1$H-NMR (CDCl$_3$) δ 1.22 (3H, t, J=7.2 Hz, CH$_3$), 1.35 (3H, d, J=7.2 Hz, CH$_3$), 2.53 (2H, t, J=6.9 Hz, CH$_2$), 2.88 (2H, t, J=6.9 Hz, CH$_2$), 3.79 (3H, s, CH$_3$O), 4.15 (2H, q, J=7.2 Hz, CH$_2$), 4.53 (1H, m, CH), 5.96 (1H, d, J=5.4 Hz, NH), 6.82-7.19 (4H, m, phenyl);
MS (ESI): m/z=280.4 (M$^+$+1).

Ethyl 2-(3,3-diphenylpropanamido)propanoate (32 h)

yield: 65%; $^1$H-NMR (CDCl$_3$) δ 1.12 (3H, d, J=7.2 Hz, CH$_3$), 1.22 (3H, t, J=7.2 Hz, CH$_3$), 2.91 (2H, m, CH$_2$), 4.12 (2H, q, J=7.2 Hz, CH$_2$), 4.43 (1H, m, CH), 4.55 (1H, m, CH), 5.8 (1H, d, J=7.2 Hz, NH), 7.15-7.29 (10H, m, phenyl);
MS (ESI): m/z=325.7 (M$^+$+1).

Ethyl 2-(2-(naphthalen-2-yl)acetamido)propanoate) (32i)

yield: 73.6%;
$^1$H-NMR (CDCl$_3$) δ 1.20 (3H, t, J=7.2 Hz, CH$_3$), 1.31 (3H, d, J=7.2 Hz, CH$_3$), 3.74 (2H, s, CH$_2$), 4.12 (2H, q, J=7.2 Hz, CH$_2$), 4.57 (1H, m, CH), 6.01 (1H, d, J=6.8 Hz, NH), 7.38-7.50 (3H, m, naphtyl), 7.73-7.85 (4H, m, naphtyl);
MS (ESI): m/z=285.8 (M$^+$+1).

13-2. Preparation of Oxazole Compound Intermediates (33a-i)

The mixture of 2 g of compounds 32a-i in anhydrous chloroform and 4 g of (14.0 mmol) phosphorus pentoxide was refluxed for 4 hrs. After cooling at room temperature, 50 mL of 20% aqueous KOH solution was added to the mixture and vigorously stirred for 30 min, followed by extracting with water and dichloromethane. The organic residue was collected and treated with Na$_2$SO$_4$. After filtration, the organic extract was concentrated under reduced pressure and subject to silica gel column chromatography (developing solvent: n-hexanes/ethyl acetate=3:1) to prepare intermediates as follows:

2-Benzyl-5-ethoxy-4-methyl-oxazole (33a)

yield: 94.1%;
$^1$H-NMR (CDCl$_3$) δ 1.29 (3H, t, J=7.2 Hz, CH$_3$), 2.01 (3H, s, CH$_3$), 3.94 (2H, s, CH$_2$), 4.05 (2H, q, J=6.9 Hz, CH$_2$), 7.23 (1H, s, phenyl-1H), 7.26 (1H, s, phenyl-2H), 7.28 (1H, s, phenyl-3H), 7.31 (1H, s, phenyl-4H), 7.34 (1H, s, phenyl-5H);
MS (MALDI-TOF): m/z=216.9 (M$^+$+1).

5-Ethoxy-4-methyl-2-phenethyl-oxazole (33b)

yield: 94.4%;
$^1$H-NMR (CDCl$_3$) δ 1.34 (3H, t, J=6.0 Hz, CH$_3$), 2.02 (3H, s, CH$_3$), 2.90 (2H, t, J=6.0 Hz, CH$_2$), 4.02 (2H, t, J=6.0 Hz, CH$_2$), 7.22 (1H, s, phenyl-1H), 7.23 (1H, s, phenyl-2H), 7.27 (1H, s, phenyl-3H), 7.28 (1H, s, phenyl-4H), 7.30 (1H, s, phenyl-5H);
MS (MALDI-TOF): m/z=232.0 (M$^+$+1).

5-Ethoxy-2-[2-(4-methoxy-phenyl)-ethyl]-4-methoxy-oxazole (33c)

yield: 91.0%;
$^1$H-NMR (CDCl$_3$) δ 1.31 (3H, t, J=7.2 Hz, CH$_3$), 2.01 (3H, s, CH$_3$), 2.83 (2H, t, J=6.0 Hz, CH$_2$), 2.90 (2H, t, J=6.0 Hz, CH$_2$), 4.05 (3H, s, OCH$_3$), 6.81 (1H, d, J=8.7 Hz, phenyl-1H), 7.10 (1H, d, J=5.4 Hz, phenyl-2H);
MS (ESI): m/z=262.4 (M$^+$+1).

5-Ethoxy-4-methyl-2-styryl-oxazole (33d)

yield: 92.2%;
$^1$H-NMR (CDCl$_3$) δ 1.36 (3H, t, J=7.2 Hz, CH$_3$), 2.11 (3H, s, CH$_3$), 4.30 (2H, t, J=7.2 Hz, CH$_2$), 6.45 (1H, d, J=15.9 Hz, CH), 6.76 (1H, d, J=17.1 Hz, CH), 7.38 (3H, s, phenyl-1H), 7.52 (2H, s, phenyl-2H);
MS (ESI): m/z=230.3 (M$^+$+1).

4-[2-(5-Ethoxy-4-methyl-oxazole-2-yl)-ethyl]-benzoic acid methyl ester (33e)

yield: 66.5%;
$^1$H-NMR (CDCl$_3$) δ 1.32 (3H, t, J=6.0 Hz, CH$_3$), 2.01 (3H, s, CH$_3$), 2.91 (2H, t, J=5.4 Hz, CH$_2$), 3.04 (2H, t, J=6.0 Hz, CH$_2$), 3.91 (3H, s, OCH$_3$), 4.06 (2H, d, J=6.0 Hz, CH$_2$), 7.27 (2H, d, J=8.1 Hz, phenyl-1H), 7.95 (2H, d, J=8.1 Hz, phenyl-2H);
MS (MALDI-TOF): m/z=290.4 (M$^+$+1).

5-Ethoxy-2-[2-(3-methoxy-phenyl)-ethyl]-4-methoxy-oxazole (33f)

yield: 46.4%;
$^1$H-NMR (CDCl$_3$) δ 1.34 (3H, t, J=6.9 Hz, CH$_3$), 2.04 (3H, s, CH$_3$), 2.90 (2H, t, J=6.9 Hz, CH$_2$), 3.01 (2H, t, J=6.9 Hz, CH$_2$), 3.81 (3H, s, CH$_3$O), 6.78 (3H, m, phenyl-1H), 7.20 (1H, m, phenyl-2H);
MS (ESI): m/z=262.3 (M$^+$+1).

5-ethoxy-2-(2-methoxyphenethyl)-4-methyloxazole (33 g)

yield: 79.8%;
$^1$H-NMR (CDCl$_3$) δ 1.32 (3H, t, J=6.9 Hz, CH$_3$), 2.03 (3H, s, CH$_3$), 2.90 (2H, t, J=6.9 Hz, CH$_2$), 3.02 (2H, t, J=6.9 Hz, CH$_2$), 3.92 (3H, s, CH$_3$O), 6.76-7.32 (4H, m, phenyl);
MS (MALDI-TOF): m/z=262.3 (M$^+$+1).

2-(2,2-diphenylethyl)-5-ethoxy-4-methyloxazole (33 h)

yield: 99%;
$^1$H-NMR (CDCl$_3$) δ 1.20 (3H, t, J=7.2 Hz, CH$_3$), 1.92 (3H, s, CH$_3$), 3.33 (2H, d, J=8.4 Hz, CH$_2$), 3.93 (2H, q, J=7.2 Hz, CH$_2$), 4.53 (1H, t, J=8.0 Hz, CH), 7.15-7.28 (10H, m, phenyl);
MS (MALDI-TOF): m/z=307.8 (M$^+$+1).

5-ethoxy-4-methyl-2-(naphthalen-2-ylmethyl)oxazole (33i)

yield: 98%;
$^1$H-NMR (CDCl$_3$) δ 1.29 (3H, t, J=6.8 Hz, CH$_3$), 2.01 (3H, s, CH$_3$), 4.04 (2H, q, J=7.2 Hz, CH$_2$), 4.10 (2H, s, CH$_2$), 7.39-7.46 (3H, m, naphtyl), 7.71-7.81 (4H, m, naphtyl);
MS (MALDI-TOF): m/z=262.3 (M$^+$+1).

13-3. Preparation of 3,4-dimethyl ester pyridine compound intermediates (34a-i)

1 mL (1.9 mmol) of dimethyl maleate was dropwisely added to 750 mg (3.4 mmol) of compounds 33a-i, refluxed for 5 hrs with stirring and cooled at room temperature. The mixture was saturated with HCl gas and concentrated under reduced pressure, yielding intermediates (34a-g) as follows:

2-Benzyl-5-hydroxy-6-methyl-pyridine-3,4-dicarboxylic acid dimethyl ester (34a)

yield: 59.1%;
$^1$H-NMR (CDCl$_3$) δ 2.84 (3H, s, CH$_3$), 3.76 (3H, s, CH$_3$O), 4.00 (3H, s, CH$_3$O), 4.42 (2H, s, CH$_2$), 7.24 (1H, s, phenyl-1H), 7.27 (1H, s, phenyl-2H), 7.28 (1H, s, phenyl-3H), 7.30 (1H, s, phenyl-4H), 7.31 (1H, s, phenyl-5H);
MS (MALDI-TOF): m/z=314.9 (M$^+$+1).

5-Hydroxy-6-methyl-2-phenethyl-pyridine-3,4-dicarboxylic acid dimethyl ester (34b)

yield: 30.1%;
$^1$H-NMR (CDCl$_3$) δ 2.64 (3H, s, CH$_3$), 3.10 (2H, t, J=7.2 Hz, CH$_2$), 3.35 (2H, t, J=7.2 Hz, CH$_2$), 4.00 (3H, s, CH$_3$O), 4.10 (3H, s, CH$_3$O), 7.20 (1H, s, phenyl-1H), 7.22 (1H, s, phenyl-2H), 7.24 (1H, s, phenyl-3H), 7.26 (1H, s, phenyl-4H), 7.29 (1H, s, phenyl-5H);
MS (ESI): m/z=330.4 (M$^+$+1).

5-Hydroxy-2-[2-(4-methoxy-phenyl)-ethyl]-6-methyl-pyridine-3,4-dicarboxylic acid dimethyl ester (34c)

yield: 37.2%;
$^1$H-NMR (CDCl$_3$) δ 3.02 (3H, s, CH$_3$), 3.04 (2H, t, J=4.8 Hz, CH$_2$), 3.32 (2H, t, J=4.8 Hz, CH$_2$), 3.79 (2H, s, CH$_2$), 4.00 (3H, s, CH$_3$O), 4.08 (3H, s, CH$_3$O), 6.83 (2H, d, J=8.7 Hz, phenyl-1H), 7.27 (1H, d, J=5.4 Hz, phenyl-2H);
MS (ESI): m/z=360.4 (M$^+$+1).

5-Hydroxy-6-methyl-2-styryl-pyridine-3,4-dicarboxylic acid dimethyl ester (34d)

yield: 23.3%;
$^1$H-NMR (CDCl$_3$) δ 2.49 (3H, s, CH$_3$), 3.83 (6H, s, 2×CH$_3$O), 6.82 (1H, d, J=15.4 Hz, olefin-CH), 7.20 (3H, m, phenyl-1H), 7.38 (2H, d, J=5.4 Hz, phenyl-2H), 7.72 (1H, t, J=15.6 Hz, olefin-CH);
MS (ESI): m/z=328.2 (M$^+$+1).

5-Hydroxy-2-[2-(4-methoxycarbonyl-phenyl)-ethyl]-6-methyl-pyridine-3,4-dicarboxylic acid dimethyl ester (34e)

yield: 33.4%;
$^1$H-NMR (CDCl$_3$) δ 2.57 (3H, s, CH$_3$), 2.90 (2H, t, J=9.0 Hz, CH$_2$), 3.04 (2H, t, J=9.3 Hz, CH$_2$), 3.86 (3H, s, CH$_3$O), 3.91 (3H, s, CH$_3$O), 3.95 (3H, s, COOCH$_3$), 7.25 (2H, d, J=8.7 Hz, phenyl-1H), 7.94 (2H, d, J=6.6 Hz, phenyl-2H);
MS (ESI): m/z=388.4 (M$^+$+1).

5-Hydroxy-2-[2-(3-methoxy-phenyl)-ethyl]-6-methyl-pyridine-3,4-dicarboxylic acid dimethyl ester (34f)

yield: 7.2%;
$^1$H-NMR (CDCl$_3$) δ 3.00 (3H, s, CH$_3$), 3.10 (2H, t, J=3.9 Hz, CH$_2$), 3.35 (2H, t, J=7.8 Hz, CH$_2$), 3.86 (2H, s, CH$_2$), 3.98 (3H, s, CH$_3$O), 4.10 (3H, s, CH$_3$O), 6.78 (1H, dd, J=7.5 Hz, 8.1 Hz, phenyl-1H), 6.90 (1 h, d, J=7.5 Hz, phenyl-2H), 7.00 (1H, s, phenyl-3H), 7.21 (1H, t, J=8.1 Hz, phenyl-4H);
MS (ESI): m/z=360.1 (M$^+$+1).

Dimethyl 5-hydroxy-2-(2-methoxyphenethyl)-6-methylpyridine-3,4-dicarboxylate (34 g)

yield: 23.2%;
$^1$H-NMR (CDCl$_3$) δ 2.58 (3H, s, CH$_3$), 2.92 (2H, t, J=7.2 Hz, CH$_2$), 2.99 (2H, t, J=7.2 Hz, CH$_2$), 3.83 (3H, s, CH$_3$O), 3.86 (3H, s, COOCH$_3$), 3.94 (3H, s, COOCH$_3$), 6.84-7.21 (4H, m, phenyl), 10.55 (1H, s, OH);
MS (ESI): m/z=340.4 (M$^+$+1).

Dimethyl 2-(2,2-diphenylethyl)-5-hydroxy-6-methylpyridine-3,4-dicarboxylate (34 h)

yield: 21%;
$^1$H-NMR (CDCl$_3$) δ 2.46 (3H, s, CH$_3$), 3.37 (2H, t, J=8.0 Hz, CH$_2$), 3.75 (3H, s, COOCH$_3$), 3.88 (3H, s, COOCH$_3$), 7.10-7.24 (1H, m, phenyl), 10.47 (1H, s, OH);
MS (ESI): m/z=406 (M$^+$+1).

Dimethyl 5-hydroxy-2-(2-methoxyphenethyl)-6-methylpyridine-3,4-dicarboxylate (34i)

yield: 23.2%;
$^1$H-NMR (CDCl$_3$) δ 2.54 (3H, s, CH$_3$), 3.72 (3H, s, COOCH$_3$), 3.92 (3H, s, COOCH$_3$), 4.21 (2H, s, CH$_2$), 7.35-7.48 (3H, m, naphtyl), 7.62-7.78 (4H, m, naphtyl), 10.57 (1H, s, OH);
MS (ESI): m/z=366.4 (M$^+$+1).

13-4. Preparation of 3,4-dicarboxy pyridine compound (35-41, 50 and 51)

20 mL of 20% aqueous KOH solution was added to 1 g (3.2 mmol) of compounds 34a-i with vigorous stirring for 6 hrs. The mixture was purified by ion-exchange resin column chromatography (Amberlite CG-50 resin) to obtain compounds 35-41, 50 and 51 as the following target substances, and their purities were determined using an analytic HPLC system:

2-Benzyl-5-hydroxy-6-methyl-pyridine-3,4-dicarboxylic acid (35)

yield: 65.9%;
$^1$H-NMR (CDCl$_3$) δ 2.28 (3H, s, CH$_3$), 3.91 (3H, s, CH$_3$O), 7.11 (1H, s, phenyl-1H), 7.13 (1H, s, phenyl-2H), 7.16 (1H, s, phenyl-3H), 7.18 (1H, s, phenyl-4H), 7.20 (1H, s, phenyl-5H);
MS (ESI): m/z=286.1 (M$^+$+1);
elementary analysis: (C$_{15}$H$_{13}$NO$_5$) C, H, N.

5-Hydroxy-6-methyl-2-phenethyl-pyridine-3,4-dicarboxylic acid (36)

yield: 69.7%;
$^1$H-NMR (CDCl$_3$) δ 2.31 (3H, s, CH$_3$), 2.84 (4H, m, 2×CH$_2$), 7.18 (1H, s, phenyl-1H), 7.22 (1H, s, phenyl-2H), 7.24 (1H, s, phenyl-3H), 7.26 (1H, s, phenyl-4H), 7.29 (1H, s, phenyl-4H), MS (ESI): m/z=300.1 (M$^+$+1);
elementary analysis: (C$_{16}$H$_{15}$NO$_5$) C, H, N.

5-Hydroxy-2-[2-(4-methoxy-phenyl)ethyl]-6-methyl-pyridine-3,4-dicarboxylic acid (37)

yield: 74.6%;
$^1$H-NMR (CDCl$_3$) δ 2.25 (3H, s, CH$_3$), 2.80 (4H, m, 2×CH$_2$), 3.80 (3H, s, CH$_3$O), 6.91 (2H, d, J=8.7 Hz, phenyl-1H), 7.21 (2H, d, J=9.0 Hz, phenyl-2H), MS (ESI): m/z=332.3 (M$^+$+1);
elementary analysis: (C$_{17}$H$_{17}$NO$_6$) C, H, N. 5-Hydroxy-6-methyl-2-styryl-pyridine-3,4-dicarboxylic acid (38).
yield: 56.0%;
$^1$H-NMR (CDCl$_3$) δ 2.42 (3H, s, CH$_3$), 7.11 (1H, t, J=16.5 Hz, olefin-CH), 7.30 (1H, t, J=16.5 Hz, olefin-CH), 7.28 (3H, m, phenyl-1H), 7.55 (2H, d, J=7.2 Hz, phenyl-2H), MS (ESI): m/z=298.1 (M$^+$+1);
elementary analysis: (C$_{16}$H$_{13}$NO$_5$) C, H, N.

2-[2-(4-Carboxy-phenyl)-ethyl]-5-hydroxy-6-methyl-pyridine-3,4-dicarboxylic acid (39)

yield: 83.8%;
$^1$H-NMR (CDCl$_3$) δ 2.38 (3H, s, CH$_3$), 2.94 (4H, m, 2×CH$_2$), 7.22 (2H, d, J=8.1 Hz, phenyl-1H), 7.72 (2H, d, J=8.1 Hz, phenyl-2H);
MS (ESI): m/z=346.3 (M$^+$+1);
elementary analysis: (C$_{17}$H$_{15}$NO$_7$) C, H, N.

5-Hydroxy-2-[2-(3-methoxy-phenyl)-ethyl]-6-methyl-pyridine-3,4-dicarboxylic acid (40)

yield: 59.3%;
$^1$H-NMR (CDCl$_3$) δ 2.34 (3H, s, CH$_3$), 2.87 (4H, m, 2×CH$_2$), 3.74 (3H, s, CH$_3$O), 6.77 (3H, m, phenyl-1H), 7.24 (2H, m, phenyl-2H);
MS (ESI): m/z=332.3 (M$^+$+1);
elementary analysis: (C$_{17}$H$_{17}$NO$_6$) C, H, N.

5-Hydroxy-2-[2-(2-methoxy-phenyl)-ethyl]-6-methyl-pyridine-3,4-dicarboxylic acid (41)

yield: 71.8%;
$^1$H-NMR (DMSO-d$_6$) δ 2.99 (3H, s, CH$_3$), 2.86 (2H, t, J=6.9 Hz, CH$_2$), 2.89 (2H, t, J=6.9 Hz, CH$_2$), 3.77 (3H, s, CH$_3$O), 6.88 (1H, t, J=7.2 Hz, phenyl-1H), 6.96 (1H, dd, J=0.9 Hz, 0.9 Hz, phenyl-2H), 7.11 (1H, dd, J=1.8 Hz, 1.8 Hz, phenyl-3H), 7.19 (1H, s, phenyl-5H);
MS (ESI): m/z=332.3 (M$^+$+1);
elementary analysis: (C$_{17}$H$_{17}$NO$_6$) C, H, N.

5-Hydroxy-6-methyl-2-(naphthalene-1-ylmethyl)pyridine-3,4-dicarboxylic acid (50)

yield: 54.5%;
$^1$H-NMR (MeOH-d$_4$) δ 2.36 (3H, s, CH$_3$), 4.22 (2H, s, CH$_2$), 7.34 (4H, m, naphtyl-4H), 7.71 (3H, m, phenyl-3H);
MS (ESI): m/z=337.3 (M$^+$+1);
elementary analysis: (C$_{19}$H$_{15}$NO$_5$) C, H, N.

2-(2,2,-diphenylethyl)5-hydroxy-6-methylpyridine-3,4-dicarboxylic acid (51)

yield: 55.6%;
$^1$H-NMR (MeOH-d$_4$) δ 2.36 (3H, s, CH$_3$), 3.38 (2H, d, J=8.0 Hz, phenyl-2H), 4.74 (H, t, J=8.0 Hz, CH), 7.19 (10H, m, diphenyl-10H);
MS (ESI): m/z=377.4 (M$^+$+1);
elementary analysis: (C$_{22}$H$_{19}$NO$_5$) C, H, N.

Example 14

General Preparation Method of 4-acetyl-3-carboxy-pyridine Derivatives (Compounds 44-49)

14-1. Preparation of 4-acetyl-3-methylester pyridine intermediates (43a-g)

Oxazole derivative intermediates prepared hereinabove, i.e., compounds of 33a-f (8.0 mmole) and 2 g (12.0 mmol) of ethyl 4-oxopent-2-enoate were mixed well with each other and heated for 10-14 hrs at 55-60° C. The intermediates (Diels-Alder adduct) were dissolved in 25 mL of ethanol and cooled to 0° C. The reaction mixture was passed through HCl gas for 20 min and stirred for 30 min at 0-10° C. and for 1 hr at room temperature. The reaction mixture was added to 100 mL of 8% aqueous sodium carbonate solution and extracted by chloroform. The organic layer was concentrated and the crude product was subject to silica gel chromatography to obtain the intermediates of compounds (43a-g) as follows:

Ethyl 4-acetyl-2-benzyl-5-hydroxy-6-methylnicotinate (43a)

yield: 22.9%;
$^1$H-NMR (CDCl$_3$) δ 1.17 (3H, t, J=6.9 Hz, CH$_3$), 2.55 (3H, s, CH$_3$-pyridine), 2.59 (3H, s, CH$_3$CO), 3.21 (2H, t, J=7.2 Hz, CH$_2$), 3.58 (2H, t, J=7.2 Hz, CH$_2$), 4.43 (2H, q, J=6.9 Hz, CH$_2$O), 7.17-7.45 (5H, m, phenyl), 11.34 (1H, s, OH);
MS (FAB+): m/z=314.3 (M$^+$+1).

Ethyl 4-acetyl-5-hydroxy-6-methyl-2-phenethylnicotinate (43b)

yield: 9.5%;
$^1$H-NMR (CDCl$_3$) δ 1.28 (3H, t, J=6.9 Hz, CH$_3$), 2.52 (3H, s, CH$_3$-pyridine), 2.56 (3H, s, CH$_3$CO), 3.00 (2H, t, J=7.2 Hz, CH$_2$), 3.23 (2H, t, J=7.2 Hz, CH$_2$), 4.41 (2H, q, J=6.9 Hz, CH$_2$O), 7.18-7.30 (5H, m, phenyl), 11.42 (1H, s, OH);
MS (MALDI-TOF): m/z=328.4 (M$^+$+1).

Ethyl 4-acetyl-5-hydroxy-2-(4-methoxyphenethyl)-6-methylnicotinate (43c)

yield: 12.8%;
$^1$H-NMR (CDCl$_3$) δ 1.34 (3H, t, J=7.2 Hz, CH$_3$), 2.52 (3H, s, CH$_3$-pyridine), 2.56 (3H, s, CH$_3$CO), 2.94 (2H, d, J=7.2 Hz, CH$_2$), 3.03 (2H, d, J=7.2 Hz, CH$_2$), 3.80 (3H, s, CH$_3$O), 4.35 (2H, q, J=7.2 Hz, CH$_2$O), 6.82 (2H, d, J=8.4 Hz, phenyl-1H+5H), 7.11 (2H, d, J=8.4 Hz, phenyl-2H+4H), 11.38 (1H, s, OH);
MS (ESI): m/z=358.3 (M$^+$+1).

(E)-ethyl 4-acetyl-5-hydroxy-6-methyl-2-styrylnicotinate (43d)

yield: 14.2%;
$^1$H-NMR (CDCl$_3$) δ 1.20 (3H, t, J=7.2 Hz, CH$_3$), 1.89 (3H, s, CH$_3$-pyridine), 2.66 (3H, s, CH$_3$CO), 4.10 (3H, q, J=7.2 Hz, CH$_2$O), 7.26-7.40 (3H, m, phenyl-2H+3H+4H), 7.65 (1H, d, J=7.2 Hz, phenyl-1H), 7.67 (1H, d, J=7.2 Hz, phenyl-5H), 7.96 (1H, d, J=15.9 Hz, =CH), 8.01 (1H, d, J=15.9 Hz, =CH);
MS (ESI): m/z=326.2 (M$^+$+1).

Ethyl 4-acetyl-5-hydroxy-2-(3-methoxyphenethyl)-6-methylnicotinate (43e)

yield: 9.5%;
$^1$H-NMR (CDCl$_3$) δ 1.21 (3H, t, J=7.2 Hz, CH$_3$), 1.85 (3H, s, CH$_3$-pyridine), 2.60 (3H, s, CH$_3$CO), 2.98 (2H, t, J=7.2 Hz, CH$_2$), 3.43 (2H, t, J=7.2 Hz, CH$_2$), 3.78 (3H, s, CH$_3$O), 6.79-6.84 (3H, m, phenyl-1H+2H+3H), 7.31 (1H, s, phenyl-5H), 11.28 (1H, b, OH);
MS (ESI): m/z=357.4 (M$^+$+1).

Ethyl 4-acetyl-5-hydroxy-2-(2-methoxyphenethyl)-6-methyl nicotinate (43f)

yield: 12.8%;
$^1$H-NMR (CDCl$_3$) δ 1.34 (3H, t, J=7.2 Hz, CH$_3$), 2.51 (3H, s, CH$_3$-pyridine), 2.56 (3H, s, CH$_3$CO), 2.96 (2H, t, J=6.9 Hz, CH$_2$), 3.40 (2H, t, J=6.9 Hz, CH$_2$), 3.81 (3H, s, CH$_3$O), 6.85-7.26 (4H, m, phenyl-1H+2H+3H+4H), 11.35 (1H, b, OH);
MS (ESI): m/z=357.4 (M$^+$+1).

14-2. Preparation of 4-acetyl-3-carboxy pyridine compounds (44-49)

40 mL of 5% KOH in methanol was added to oxazole derivative intermediates as prepared hereinabove, i.e., compounds of 43a-f (0.84 mmole) and stirred for 2-3 hrs at the room temperature. The reaction mixture was acidified with 1:1 HCl and extracted with chloroform. The organic layer was dried by anhydrous sodium sulfate and concentrated. The crude product was purified by silica gel chromatography (developing solvent: ethyl acetate/n-hexanes solvent system) to obtain the compounds (44-49) as follows:

4-acetyl-2-benzyl-5-hydroxy-6-methylnicotinic acid (44)

yield: 82.1%;
$^1$H-NMR (DMSO-d$_6$) δ 2.55 (3H, s, CH$_3$-pyridine), 2.59 (3H, s, CH$_3$CO), 3.21 (2H, t, J=7.2 Hz, CH$_2$), 7.17-7.45 (5H, m, phenyl), 11.30 (1H, s, OH);
MS (FAB+): m/z=286.2 (M$^+$+1);
elementary analysis: (C$_{16}$H$_{15}$NO$_4$) C, H, N.

4-acetyl-5-hydroxy-6-methyl-2-phenethylnicotinic acid (45)

yield: 78.9%;
$^1$H-NMR (DMSO-d$_6$) δ 2.52 (3H, s, CH$_3$-pyridine), 2.56 (3H, s, CH$_3$CO), 3.00 (2H, t, J=7.2 Hz, CH$_2$), 3.23 (2H, t, J=7.2 Hz, CH$_2$) 7.18-7.30 (5H, m, phenyl), 11.42 (1H, s, OH);
MS (ESI): m/z=300.2 (M$^+$+1);
elementary analysis: (C$_{17}$H$_{17}$NO$_4$) C, H, N.

4-acetyl-5-hydroxy-2-(4-methoxyphenethyl)-6-methylnicotinic acid (46)

yield: 89.8%;
$^1$H-NMR (DMSO-d$_6$) δ 2.52 (3H, s, CH$_3$-pyridine), 2.56 (3H, s, CH$_3$CO), 2.94 (2H, d, J=7.2 Hz, CH$_2$), 3.03 (2H, d, J=7.2 Hz, CH$_2$), 3.80 (3H, s, CH$_3$O), 6.82 (2H, d, J=8.4 Hz, phenyl-1H+5H), 7.11 (2H, d, J=8.4 Hz, phenyl-2H+4H), 11.38 (1H, s, OH);
MS (ESI): m/z=330.4 (M$^+$+1);
elementary analysis: (C$_{18}$H$_{19}$NO$_5$) C, H, N.

(E)-4-acetyl-5-hydroxy-6-methyl-2-styrylnicotinic acid (47)

yield: 83.6%;
$^1$H-NMR (DMSO-d$_6$) δ 1.89 (3H, s, CH$_3$-pyridine), 2.66 (3H, s, CH$_3$CO), 7.26-7.40 (3H, m, phenyl-2H+3H+4H), 7.65 (1H, d, J=7.2 Hz, phenyl-1H), 7.67 (1H, d, J=7.2 Hz, phenyl-5H), 7.96 (1H, d, J=15.9 Hz, =CH), 8.01 (1H, d, J=15.9 Hz, =CH);
MS (ESI): m/z=298.2 (M$^+$+1);
elementary analysis: (C$_{17}$H$_{15}$NO$_4$) C, H, N.

(E)-4-acetyl-5-hydroxy-2-(3-methoxystyryl)-6-methylnicotinic acid (48)

yield: 69.9%;
$^1$H-NMR (DMSO-d$_6$) δ 1.85 (3H, s, CH$_3$-pyridine), 2.60 (3H, s, CH$_3$CO), 2.98 (2H, t, J=7.2 Hz, CH$_2$), 3.43 (2H, t, J=7.2 Hz, CH$_2$), 3.78 (3H, s, CH$_3$O), 6.79-6.84 (3H, m, phenyl-1H+2H+3H), 7.31 (1H, s, phenyl-5H), 11.28 (1H, b, OH);
MS (ESI): m/z=330.2 (M$^+$+1);
elementary analysis: (C$_{18}$H$_{19}$NO$_5$) C, H, N.

(E)-4-acetyl-5-hydroxy-2-(2-methoxystyryl)-6-methylnicotinic acid (49)

yield: 75.2%;
$^1$H-NMR (DMSO-d$_6$) δ 2.51 (3H, s, CH$_3$-pyridine), 2.56 (3H, s, CH$_3$CO), 2.96 (2H, t, J=6.9 Hz, CH$_2$), 3.40 (2H, t, J=6.9 Hz, CH$_2$), 3.81 (3H, s, CH$_3$O), 6.85-7.26 (4H, m, phenyl-1H+2H+3H+4H), 11.35 (1H, b, OH), MS (ESI): 330.4 (M$^+$+1);
elementary analysis: (C$_{18}$H$_{19}$NO$_5$) C, H, N.

Example 15

General Preparation Method of 4-formyl-3-carboxypyridine Derivatives (Compounds 61 and 64)

15-1. Preparation of Dimethyl 5-[benzyloxy]-2-[4-methoxyphenethyl]-6-methylpyridine-3,4-dicarboxylate) intermediate (52)

192 μL (1.7 mmol) of benzyl bromide was dropwisely added to 480 mg (1.4 mmol) of the compound 34d in anhydrous acetone, refluxed for 2 hrs and cooled at room temperature. After neutralization with ammonium chloride (NH$_4$Cl), the resultant was extracted with dichloromethane. The organic residue was collected and treated with Na$_2$SO$_4$. After filtration, the organic extract was concentrated under reduced pressure and subject to silica gel column chromatography (developing solvent: n-hexanes/ethyl acetate=3:1) to obtain the intermediate as follows:
yield: 83.5%,
$^1$H-NMR (CDCl$_3$) δ 2.56 (3H, s, CH$_3$-pyridine), 2.94 (2H, m, CH$_2$), 3.18 (2H, m, CH$_2$), 3.78 (3H, s, CH$_3$O), 3.83 (3H, s, CH$_3$O), 3.85 (3H, s, CH$_3$O), 4.95 (2H, s, CH$_2$-benzyl), 6.83 (2H, d, J=8.4 Hz, phenyl), 7.16 (2H, d, J=8.8 Hz, phenyl), 7.41 (5H, m, phenyl),
MS (ESI): m/z=449.5 (M$^+$+1),
elementary analysis: (C$_{27}$H$_{26}$NO$_6$) C, H, N.

15-2. Preparation of {5-[benzyloxy]-2-[4-methoxyphenethyl)-6-methylpyridine-3,4-diyl}dimethanol) intermediate (53)

12 μL (0.26 mmol) of lithium aluminum hydride (LAIN was dropwisely added to 20 mg (0.04 mmol) of the compound 52 in anhydrous THF (tetrahydrofuran) and stirred for 2 hrs. After neutralization with ammonium chloride (NH$_4$Cl), the resultant was extracted with dichloromethane. The organic residue was collected and treated with Na$_2$SO$_4$. After filtration, the organic extract was concentrated under reduced pressure and subject to silica gel column chromatography (developing solvent: chloroform/methanol=100:1) to obtain the intermediate as follows:

yield: 47.5%, $^1$H-NMR (CDCl$_3$) δ: 2.54 (3H, s, CH$_3$-pyridine), 2.95 (2H, m, CH$_2$), 3.10 (2H, m, CH$_2$), 3.76 (3H, s, CH$_3$O), 4.55 (2H, s, CH$_2$OH), 4.68 (2H, s, CH$_2$OH), 4.91 (2H, s, CH$_2$-benzyl), 6.78 (2H, d, J=8.8 Hz, phenyl), 7.04 (2H, d, J=8.4 Hz, phenyl), 7.41 (5H, m, phenyl), MS (ESI): m/z=394.4 (M$^+$+1), elementary analysis: (C$_{24}$H$_{27}$NO$_4$) C, H, N.

15-3. Preparation of {5-hydroxy-2-[4-methoxyphenethyl]-6-methylpyridine-3,4-diyl}dimethanol) intermediate (54)

20 mg (0.26 mmol) of Pd/C was added to 65 mg (0.16 mmol) of the compound 53 in anhydrous methanol and stirred for 15 min at 0° C. under hydrogen atmosphere. The mixture was filtrated through celatum bed. The filtrated was evaporated under reduced pressure and subject to silica gel column chromatography (developing solvent: chloroform/methanol=50:1) to obtain the intermediate as follows:

yield: 90%, $^1$H-NMR (CDCl$_3$) δ: 2.47 (3H, s, CH$_3$-pyridine), 2.88 (2H, m, CH$_2$), 3.01 (2H, m, CH$_2$), 3.76 (3H, s, CH$_3$O), 4.36 (2H, s, CH$_2$OH), 4.98 (2H, s, CH$_2$OH), 6.75 (2H, d, J=8.4 Hz, phenyl), 6.95 (2H, d, J=8.4 Hz, phenyl), MS (ESI): m/z=304.4 (M$^+$+1), elementary analysis: (C$_{17}$H$_{21}$NO$_4$) C, H, N.

15-4. Preparation of (6-(4-methoxyphenethyl)-2,2,8-trimethyl-4H-[1,3]dioxino[4,5-c]pyridin-5-yl)methanol intermediate (55)

Solid form of intermediate was prepared by the similar manner to the method disclosed in Example 1-2.

yield: 62%, $^1$H-NMR (CDCl$_3$) δ 1.55 (6H, s, 2CH$_3$), 2.41 (3H, s, CH$_3$-pyridine), 2.92 (2H, m, CH$_2$), 3.01 (2H, m, CH$_2$), 3.75 (3H, s, CH$_3$O), 4.31 (2H, s, CH$_2$OH), 4.88 (2H, s, CH$_2$OH), 6.77 (2H, d, J=8.4 Hz, phenyl), 6.96 (2H, d, J=8.4 Hz, phenyl), MS (ESI):

m/z=344.4 (M$^+$+1), elementary analysis: (C$_{20}$H$_{25}$NO$_4$) C, H, N.

15-5. Preparation of 6-(4-methoxyphenethyl)-2,2,8-trimethyl-4H-[1,3]dioxino[4,5-c]pyridine-5-carbaldehyde intermediate (56)

Solid form of intermediate was prepared by the similar manner to the method disclosed in Example 1-3.

yield: 96%, $^1$H-NMR (CDCl$_3$) δ 1.55 (6H, s, 2CH$_3$), 2.47 (3H, s, CH$_3$-pyridine), 2.94 (2H, m, CH$_2$), 3.30 (2H, m, CH$_2$), 3.77 (3H, s, CH$_3$O), 5.08 (2H, s, CH$_2$OH), 6.78 (2H, d, J=8.4 Hz, phenyl), 7.03 (2H, d, J=8.4 Hz, phenyl), 10.19 (H, s, CHO), MS (ESI): m/z=342.2 (M$^+$+1), elementary analysis: (C$_{20}$H$_{23}$NO$_4$) C, H, N.

15-6. Preparation of {(E)-ethyl 3-(6-(4-methoxyphenethyl)-2,2,8-trimethyl-4H-[1,3]dioxino[4,5-c]pyridin-5-yl)acrylate} intermediate (57)

Solid form of intermediate was prepared by the similar manner to the method disclosed in Example 1-5.

yield: 93%, $^1$H-NMR (CDCl$_3$) δ 1.32 (3H, t, J=7.2 Hz CH$_3$), 1.55 (6H, s, 2CH$_3$), 2.42 (3H, s, CH$_3$-pyridine), 2.88 (2H, m, CH$_2$), 2.97 (2H, m, CH$_2$), 3.77 (3H, s, CH$_3$O), 4.25 (2H, q, J=7.2 Hz, CH$_2$), 4.75 (2H, s, CH$_2$OH), 5.81 (1H, d, J=16.4 Hz, =CH), 6.77 (2H, d, J=8.8 Hz, phenyl), 7.04 (2H, d, J=8.4 Hz, phenyl), 7.54 (1H, d, J=16.4 Hz, =CH), MS (ESI): m/z=412.3 (M$^+$+1), elementary analysis: (C$_{24}$H$_{29}$NO$_5$) C, H, N.

15-7. Preparation of {(E)-ethyl 3-(5-hydroxy-4-(hydroxymethyl)-2-(4-methoxyphenethyl)-6-methylpyridin-3-yl)acrylate} intermediate (58)

Solid form of intermediate was prepared by the similar manner to the method disclosed in Example 1-6.

yield: 83%, $^1$H-NMR (CDCl$_3$) δ 1.30 (3H, t, J=7.2 Hz CH$_3$), 2.45 (3H, s, CH$_3$-pyridine), 2.82 (2H, m, CH$_2$), 2.87 (2H, m, CH$_2$), 3.76 (3H, s, CH$_3$O), 4.21 (2H, q, J=7.2 Hz, CH$_2$), 4.90 (2H, s, CH$_2$OH), 5.61 (1H, d, J=16.4 Hz, =CH), 6.75 (2H, d, J=8.8 Hz, phenyl), 6.99 (2H, d, J=8.4 Hz, phenyl), 7.54 (1H, d, J=16.4 Hz, =CH), MS (ESI): m/z=372.1 (M$^+$+1), elementary analysis: (C$_{21}$H$_{25}$NO$_5$) C, H, N.

15-7. Preparation of {ethyl 3-(5-hydroxy-4-(hydroxymethyl)-2-(4-methoxyphenethyl)-6-methylpyridin-3-yl)propanoate} intermediate (59)

Solid form of intermediate was prepared by the similar manner to the method disclosed in Example 1-6.

yield: 84%, $^1$H-NMR (CDCl$_3$) δ 1.18 (3H, t, J=7.2 Hz CH$_3$), 2.31 (2H, t, J=7.6 Hz, CH$_2$), 2.45 (3H, s, CH$_3$-pyridine), 2.75 (2H, t, J=7.6 Hz, CH$_2$), 2.82 (2H, m, CH$_2$), 2.91 (2H, m, CH$_2$), 3.77 (3H, s, CH$_3$O), 4.05 (2H, q, J=7.2 Hz, CH$_2$), 4.94 (2H, s, CH$_2$OH), 6.78 (2H, d, J=8.8 Hz, phenyl), 7.54 (2H, d, J=8.8 Hz, phenyl), MS (ESI): m/z=373.9 (M$^+$+1), elementary analysis: (C$_{21}$H$_{22}$NO$_5$) C, H, N.

15-8. Preparation of {ethyl 3-(4-formyl-5-hydroxy-2-(4-methoxyphenethyl)-6-methylpyridin-3-yl)propanoate} intermediate (60)

Solid form of intermediate was prepared by the similar manner to the method disclosed in Example 1-7.

yield: 81%, $^1$H-NMR (CDCl$_3$) δ 1.21 (3H, t, J=7.2 Hz CH$_3$), 2.40 (2H, t, J=8.0 Hz, CH$_2$), 2.52 (3H, s, CH$_3$-pyridine), 2.98 (4H, m, 2CH$_2$), 3.10 (2H, t, J=8.0 Hz, CH$_2$), 3.77 (3H, s, CH$_3$O), 4.11 (2H, q, J=7.2 Hz, CH$_2$), 6.78 (2H, d, J=8.8 Hz, phenyl), 7.04 (2H, d, J=8.8 Hz, phenyl), 10.42 (1H, s, CHO). MS (ESI): m/z=371.9 (M$^+$+1), elementary analysis: (C$_{21}$H$_{25}$NO$_5$) C, H, N.

15-9. Preparation of {3-(4-formyl-5-hydroxy-2-(4-methoxyphenethyl)-6-methylpyridin-3-yl)propanoic acid} compound (61)

Solid form of intermediate was prepared by the similar manner to the method disclosed in Example 1-8.
yield: 32%,
$^1$H-NMR (CDCl$_3$) δ 2.43 (2H, t, J=8.4 Hz, CH$_2$), 2.52 (3H, s, CH$_3$-pyridine), 2.98 (4H, m, 2CH$_2$), 3.08 (2H, t, J=8.4 Hz, CH$_2$), 3.76 (3H, s, CH$_3$O), 6.78 (2H, d, J=8.8 Hz, phenyl), 7.04 (2H, d, J=8.8 Hz, phenyl), 10.41 (1H, s, CHO).
MS (ESI): m/z=343.9 (M$^+$+1),
elementary analysis: (C$_{19}$H$_{21}$NO$_5$) C, H, N.

15-9. Preparation of {(E)-3-(6-(4-methoxyphenethyl)-2,2,8-trimethyl-4H-[1,3]dioxino [4,5-c]pyridin-5-yl)acrylic acid} intermediate (62)

Solid form of intermediate was prepared by the similar manner to the method disclosed in Example 1-8.
yield: 90%,
$^1$H-NMR (CDCl$_3$) δ 1.55 (6H, s, 2CH$_3$), 2.43 (3H, s, CH$_3$-pyridine), 2.89 (2H, m, CH$_2$), 3.02 (2H, m, CH$_2$), 3.75 (3H, s, CH$_3$O), 4.77 (2H, s, CH$_2$), 5.84 (1H, d, J=16.4 Hz, =CH), 6.77 (2H, d, J=8.4 Hz, phenyl), 7.04 (2H, d, J=8.0 Hz, phenyl), 7.62 (1H, d, J=16.4 Hz, =CH). MS (ESI): m/z=381.9 (M$^+$−1),
elementary analysis: (C$_{22}$H$_{25}$NO$_5$) C, H, N.

15-10. Preparation of {(E)-3-(5-hydroxy-4-(hydroxymethyl)-2-(4-methoxyphenethyl)-6-methylpyridin-3-yl)acrylic acid} intermediate (63)

Solid form of intermediate was prepared by the similar manner to the method disclosed in Example 1-5.
yield: 43%,
$^1$H-NMR (CDCl$_3$) δ 2.37 (3H, s, CH$_3$-pyridine), 2.70 (2H, m, CH$_2$), 2.81 (2H, m, CH$_2$), 3.67 (3H, s, CH$_3$O), 4.72 (2H, s, CH$_2$), 5.67 (1H, d, J=16.4 Hz, =CH), 6.65 (2H, d, J=8.0 Hz, phenyl), 6.95 (2H, d, J=8.0 Hz, phenyl), 7.43 (1H, d, J=16.0 Hz, =CH),
MS (ESI): m/z=342.9 (M$^+$−1),
elementary analysis: (C$_{19}$H$_{21}$NO$_5$) C, H, N.

15-11. Preparation of {(E)-3-(4-formyl-5-hydroxy-2-(4-methoxyphenethyl)-6-methylpyridin-3-yl)acrylic acid} compound (64)

Solid form of intermediate was prepared by the similar manner to the method disclosed in Example 1-7.
yield: 27%,
$^1$H-NMR (CDCl$_3$) δ 2.59 (3H, s, CH$_3$-pyridine), 2.93 (2H, m, CH$_2$), 3.03 (2H, m, CH$_2$), 3.75 (3H, s, CH$_3$O), 5.73 (1H, d, J=16.0 Hz, =CH), 6.76 (2H, d, J=8.4 Hz, phenyl), 6.96 (2H, d, J=8.4 Hz, phenyl), 7.73 (1H, d, J=16.0 Hz, =CH), 10.01 (1H, s, CHO),
MS (ESI): m/z=339.7 (M$^+$−1),
elementary analysis: (C$_{19}$H$_{19}$NO$_5$) C, H, N.

15-12. Preparation of {6-(4-methoxyphenethyl)-2,2,8-trimethyl-4H-[1,3]dioxino[4,5-c]pyridine-5-carboxylic acid} intermediate (65)

Solid form of intermediate was prepared by the similar manner to the method disclosed in Example 2.
yield: 80%,
$^1$H-NMR (CDCl$_3$) δ 1.55 (6H, s, 2CH$_3$), 2.47 (3H, s, CH$_3$-pyridine), 2.93 (2H, m, CH$_2$), 3.11 (2H, m, CH$_2$), 3.76 (3H, s, CH$_3$O), 5.07 (2H, s, CH$_2$OH), 6.77 (2H, d, J=8.4 Hz, phenyl), 7.01 (2H, d, J=8.4 Hz, phenyl),
MS (ESI): m/z=358.2 (M$^+$+1),
elementary analysis: (C$_{20}$H$_{23}$NO$_5$) C, H, N.

15-13. Preparation of {5-hydroxy-4-(hydroxymethyl)-2-(4-methoxyphenethyl)-6-methylnicotinic acid} intermediate (66)

Solid form of intermediate was prepared by the similar manner to the method disclosed in Example 1-6.
yield: 80%,
$^1$H-NMR (CDCl$_3$) δ 2.47 (3H, s, CH$_3$-pyridine), 2.94 (2H, m, CH$_2$), 3.30 (2H, m, CH$_2$), 3.77 (3H, s, CH$_3$O), 5.08 (2H, s, CH$_2$OH), 6.78 (2H, d, J=8.4 Hz, phenyl), 7.03 (2H, d, J=8.4 Hz, phenyl),
MS (ESI): m/z=318.3 (M$^+$+1),
elementary analysis: (C$_{22}$H$_{29}$NO$_5$) C, H, N.

15-14. Preparation of {4-formyl-5-hydroxy-2-(4-methoxyphenethyl)-6-methylnicotinic acid} compound (67)

Solid form of intermediate was prepared by the similar manner to the method disclosed in Example 1-7.
yield: 27%,
$^1$H-NMR (CDCl$_3$) δ 2.59 (3H, s, CH$_3$-pyridine), 2.93 (2H, m, CH$_2$), 3.03 (2H, m, CH$_2$), 3.75 (3H, s, CH$_3$O), 6.76 (2H, d, J=8.4 Hz, phenyl), 6.96 (2H, d, J=8.4 Hz, phenyl), 10.03 (1H, s, CHO),
MS (ESI): m/z=316.7 (M$^+$−1),
elementary analysis: (C$_{12}$H$_{12}$NO$_5$) C, H, N.

Experiment 1

Receptor Antagonism Test

For examination of effects on (1) antagonistic activity at recombinant mouse P2X$_1$ and human P2X$_3$ receptors and (2) ethidium$^+$ accumulation at human P2X$_7$ receptor of compounds as prepared hereinabove example, we applied measurement methods as previously disclosed in a variety of publications to perform experiments as follows (Song-Yi Lee et al 2006):

1-1. Antagonistic Activity at Recombinant Mouse P2X$_1$ and Human P2X$_3$ Receptors

*Xenopus* oocytes were harvested and prepared with method as previously described in publications. Defolliculated oocytes were injected cytosolically with mouse P2X$_1$ and human P2X$_3$ receptor cRNA (40 mL, 1 μg/mL), respectively, incubated for 24 hrs at 18° C. in Barth's solution and kept for up to 12 days at 4° C. until used in electrophysiological experiments. ATP-activated membrane currents (V$_h$=−70 mV) were recorded from cRNA-injected oocytes using the twin-electrode voltage-clamp technique (Axoclamp 2B amplifier). Voltage recording (1-2 MΩ tip resistance) and current-recording microelectrodes (5 MΩ tip resistance) were filled with 3.0 M KCl. Oocytes were held in an electrophysiological chamber and superfused with Ringer's solution (5 mL/min, at 18° C.) containing (mM) NaCl, 110; KCl, 2.5; HEPES, 5; BaCl$_2$, 1.8, adjusted to pH 7.5. ATP was superfused over the oocytes for 60-120s then washed out for a period of 20 min. For inhibition curves, data were normalized to the current evoked by ATP, at pH 7.5. Test substances were added for 20 min prior to ATP exposure; all peptides were tested for reversibility of their effects. The concentration required to inhibit the ATP response by 50% (IC$_{50}$) was taken from Hill plots constructed using the formula: log(I/I$_{max}$−1), where I is the current evoked by ATP in the presence of an antagonist. Data are presented as mean±SEM (n=4) for the data from different batches of oocytes.

1-2. Ethidium$^+$ Accumulation Assay at Human P2X$_7$ Receptors

Human P2X$_7$-expressing HEK293 cells were grown as monolayer culture at 37° C. in a humidified atmosphere of 5% $CO_2$, DMEM supplemented with 10% fetal bovine serum. Cells were harvested with treatment of Trypsin/EDTA solution, collected by centrifugation (200 g for 5 min).

The cells were resuspended at 2.5×10$^6$ cells/mL in assay buffers, consisting of (in mM) HEPES 10, KCl 140, glucose 5, EDTA 1 (pH 7.4), and then ethidium bromide (100 μM) was added. Cell suspensions were added to 96 well plates containing the P2X$_7$ receptor agonist, ATP or BzATP, at 2×10$^5$ cells/wells. Plates were incubated at 37° C. for 120 min and cellular accumulation of ethidium$^+$ was determined by measuring fluorescence with Bio-Tek instrument FL600 fluorescent plate reader (excitation wavelength of 530 nm and emission wavelength of 590 nm). When the effects of antagonists, such as PPADS, KN62, and test peptides were studied, antagonists were treated together with agonist without pre-incubation.

The 5'-phosphate group of pyridoxal-5-phosphate (hereinafter referred to as PDP, IC$_{50}$: approximately 10 μM) well-known as an antagonist to agonist-induced cation influx in the recombinant P2X$_1$ receptor was replaced with carboxylic acid for selective antagonistic activity against subtypes (see Reaction schemes 1-3), yielding antagonist compounds 13, 14, 17, 18, 22, and 23 having selective-antagonistic activity to P2 receptor subtypes. Among them, the compounds and 14 were analyzed to exhibit equal to or higher antagonistic activity than PDP to mouse P2X$_1$ and human P2X$_3$ receptors (see Table 1).

The compounds 25, 27 and 29 in the compounds 24-29 synthesized by azo coupling reaction of the compounds 13 and 14 were evaluated to have more powerful antagonistic activity to mouse P2X$_1$ than human P2X$_3$ receptor. The compound 25 in which azophenyl group was replaced with 2',5'-disulfonic acid group was shown to inhibit ion current by 60% to mouse P2X$_1$ receptor at the 100 nM concentration. The compounds 24 and 28 were further analyzed for a concentration-dependent antagonistic action. The compound 24 was revealed to show a concentration-dependent inhibitory activity to the ATP-induced ion current in mouse P2X$_1$ receptor (see FIG. 1a)

In the B panel of FIG. 1, IC$_{50}$ values and Hill coefficient are as follows: [(■) compound 24, 70.54±2.72, −1.13±0.40; (●) compound 28, 130.26±13.61, −1.20±0.45., and (▲) compound 3, 30.71±5.12, −1.09±0.13]. In C of FIG. 1, IC$_{50}$ value and Hill coefficient are as follows: [(■) compound 24, 105.47±17.49, −1.18±0.25; (●) compound 28, 79.75±1.21, −1.08±0.02., and (▲) compound 3, 96.22±20.98, −1.11±0.27].

Figure 2:
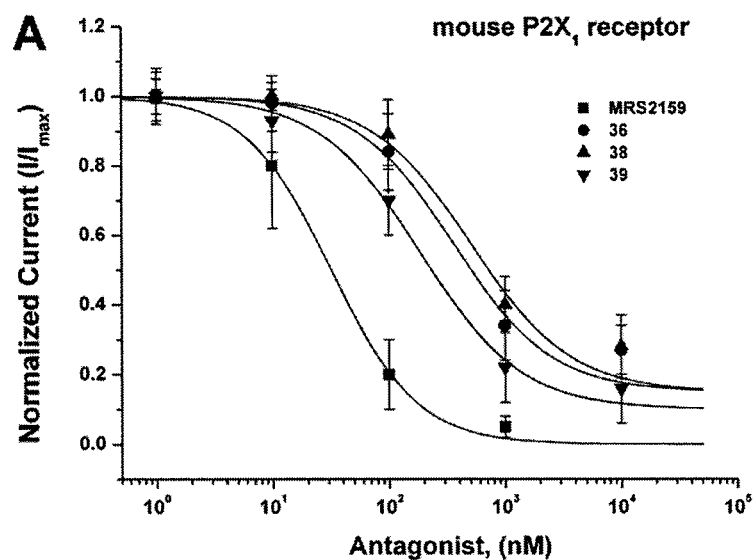
FIG. 2A shows the concentration-inhibitory curves of MRS2159 (■), 36 (●), 38 (▲) and 39 (▼) for mouse $P2X_1$ receptor. The continuous line for ATP is fit to the data using the equation: $I=I_{max}/(1+IC_{50}/L)^{nH}$, where I is the actual current for a ligand concentration (L), nH is the Hill coefficient and $I_{max}$ is the maximal current.
FIG. 2B shows the concentration-inhibitory curves of A-317491 (■), 36 (●), 38 (▲) and 39 (▼) for human $P2X_3$ receptor (C). The continuous line for ATP is fit to the data using the equation: $I=I_{max}(1+IC_{50}/L)^{nH}$, where I is the actual current for a ligand concentration (L), nH is the Hill coefficient and $I_{max}$ is the maximal current.
Figure 2:
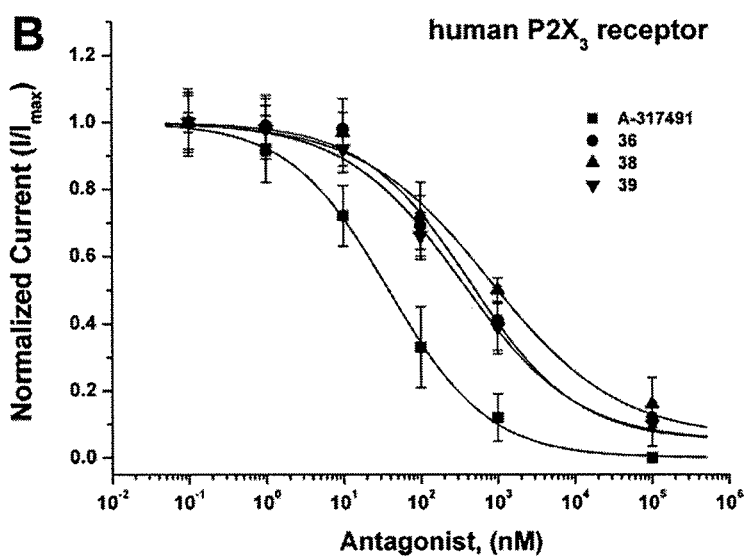

FIGS. 2B and 2C show the concentration-response curves for iso PPADS 3, compound 24 and compound 28. IC$_{50}$ value for 24 hrs in mouse P2X$_1$ and human P2X$_3$ receptors are 70 nM and 105 nM, respectively. IC$_{50}$ value for compound 28 in mouse P2X$_1$ and human P2X$_3$ receptor are 130 nM and 80 nM, respectively.

In 2A, IC$_{50}$ values were 32 nM (MRS2159); 361 nM (36); 509 nM (38); and 186 nM (39), respectively and Hill coefficient were −1.13±0.20 (MRS2159); −1.03±0.21 (36); −0.98±0.11 (38); and −1.00±0.09 (39), respectively. Each value is the mean±SEM of four (4) observations. The recordings were carried out at a holding potential (70 mV) with 2 μM ATP.

PPADS and isoPPADS are likely to degrade at room temperature, because the azo (—N=N—) linkage to pyridoxal and phenyl moiety is chemically unstable. For that reason, we developed new PPADS analogues in such a manner that the pyridoxal moiety was converted to either 3,4-dicarboxypyridine or 4-acetyl-3-carboxypyridine analogue, and then these compounds were tested for effects on mouse P2X$_1$, human P2X$_3$ and human P2X$_7$ receptors. As a result, the compound 44 was analyzed to show inhibitory effect to mouse P2X$_1$ receptor by 46% in the concentration of 10 μM. The compound 45 substituted with phenylethyl group was evaluated to exhibit more powerful activity to mouse P2X$_1$ and human P2X$_3$ receptors than the compound 45 substituted with benzyl group. The compound 46 containing 4-methoxyphenethyl group was examined to show more excellent antagonistic activity than either the compound 48 containing 3-methoxyphenethyl or the compound 49 containing 2-methoxyphenethyl.

The compounds 35-41 as 3,4-dicarboxypyridine analogues exhibited more powerful antagonistic activity to mouse P2X$_1$ and P2X$_3$ receptors than the compounds 44-49 as 4-acetyl-3-carboxypyridine analogues.

Phenethyl group compound 36, 4-methoxyphenethyl group compound 37 and 4-carboxyphenethyl compound 39 exhibited inhibitory effects to mouse P2X$_1$ r receptor by 77%, 78% and 82%, respectively in concentration of 10 μM.

FIG. 2A shows the concentration-response curves for MRS2159, the compounds 36, 38 and 39. IC$_{50}$ values for the compounds 36, 38 and 39 were 361 nM, 509 nM and 186 nM, respectively. The compounds 36, 38, and 39 were less effective than well-known antagonist, A-317491 in antagonistic activity. In FIG. 2B, IC$_{50}$ values were 38 nM (A-317491); 432 nM (36); 782 nM (38); and 339 nM (39) and Hill coefficient were −0.68±0.18 (A-317491); −0.63±0.20 (36); −0.52±0.12 (38); and −0.58±0.27 (39), respectively. Each value is represented as the mean±SEM of four (4) observations. The recordings were carried out at a holding potential (70 mV) with 2 μM ATP.

The compounds 36, 38 and 39 in concentration of 100 nM showed 38.3%, 19.2% and 34.0% inhibition, respectively. Some of compounds showed lower activity compared to conventional antagonists MRS2159 and A-317491. However, the compounds of the present invention are more druggable since they have potential antagonistic activity, stable acidity group instead of acidity groups with excessively higher polarity and stable carbon-carbon chain instead of unstable azo (—N=N—) linkage.

The shortcoming of conventional antagonist PPADS is its irreversible blocking activity to P2 receptor; however, the advantage of the compounds of the present invention is their reversible activity. Especially, the compound 39 showed approximately 95% recovery rate after 20 min.

TABLE 1

Antagonistic effects of pyridine derivatives to mouse P2X$_1$ and human P2X$_3$ receptors (1)

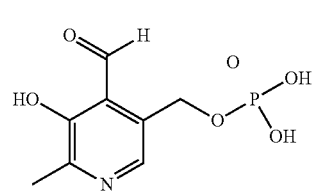

TABLE 1-continued
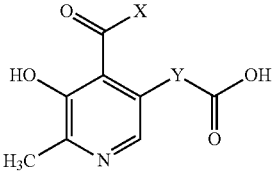
(13, 14, 17, 18)
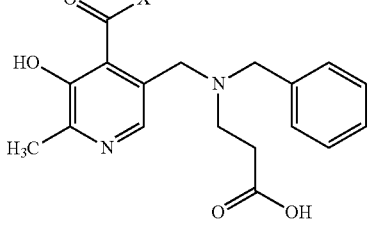
(22, 33)
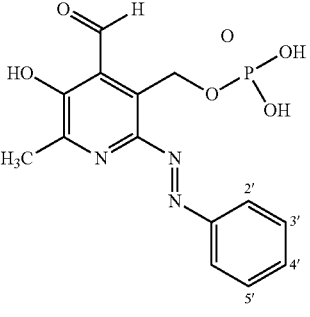
(3)
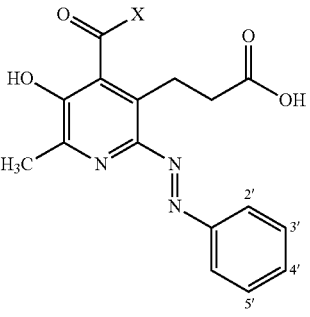
(24-29)
| compd | Positions | | | | | | % inhibition | |
| --- | --- | --- | --- | --- | --- | --- | --- | --- |
| | 2' | 3' | 4' | 5' | X | Y | mP2X$_1$[a] | hP2X$_3$[a] |
| 1[b] (pyridoxal phosphate) | | | | | | | 13.2 ± 3.1% | 20.1 ± 4.2% |
| 13[b] | | | | | H | CH$_2$CH$_2$ | 19.5 ± 5.1% | 22.3 ± 8.1% |
| 14[b] | | | | | OH | CH$_2$CH$_2$ | 14.8 ± 1.7% | 15.2 ± 7.7% |
| 17[b] | | | | | H | CH=CH | 7.4 ± 1.9% | 9.3 ± 2.3% |
| 18[b] | | | | | OH | CH=CH | inactive | inactive |
| 22[b] | | | | | H | | inactive | inactive |
| 23[b] | | | | | OH | | inactive | inactive |
| 3[c] (IsoPPADS) | SO$_3$H | H | H | SO$_3$H | | | 62.4 ± 3.1% | 48.3 ± 5.6% |
| 24[c] | SO$_3$H | H | H | SO$_3$H | H | | 58.6 ± 4.5% | 40.1 ± 8.4% |
| 25[c] | SO$_3$H | H | H | SO$_3$H | OH | | 60.2 ± 4.9% | 45.7 ± 10.8% |
| 26[c] | H | H | SO$_3$H | H | H | | 41.8 ± 9.8% | 46.5 ± 11.2% |
| 27[c] | H | H | SO$_3$H | H | OH | | 57.6 ± 8.8% | 37.6 ± 6.9% |

TABLE 1-continued

| | | | | | | | |
|---|---|---|---|---|---|---|---|
| 28[c] | | H | H | CO₂H | H | H | 48.5 ± 9.5% | 56.3 ± 8.8% |
| 29[c] | | H | H | CO₂H | H | OH | 51.7 ± 7.4% | 25.7 ± 6.9% |

[a]The ion current was induced by 2 μM ATP at the recombinant P2X receptors expressed in *Xenopus* oocytes and % inhibition of the ion current by 10 μM and 100 nM compounds was measured for mouse P2X$_1$ and human P2X$_3$ receptors, respectively (mean ± SEM, n = 4).

[b]10 μM of compounds were tested.

[c]100 nM of compounds were tested.

TABLE 2

Antagonistic effects of 3,4-dicarboxypyridine, 4-acetyl-3-carboxy pyridine, and 4-formyl-3-carboxy pyridine derivatives at mouse P2X$_1$, human P2X$_3$ and human P2X$_7$ receptors

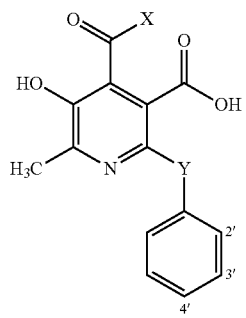

| | Positions | | | | | % inhibition | | |
|---|---|---|---|---|---|---|---|---|
| compd | 2' | 3' | 4' | X | Y | mP2X1[a] | hP2X3[a] | hP2X7[b] |
| 35 | H | H | H | OH | CH₂ | 54.2 ± 10.6% | 31.4 ± 6.2% | inactive |
| 36 | H | H | H | OH | CH₂CH₂ | 73.4 ± 9.7% | 51.0 ± 9.8% | inactive |
| 37 | H | H | OCH₃ | OH | CH₂CH₂ | 77.0 ± 3.8% | 59.8 ± 4.6% | inactive |
| 38 | H | H | H | OH | CH=CH | 71.4 ± 4.3% | 48.4 ± 9.0% | inactive |
| 39 | H | H | CO₂H | OH | CH₂CH₂ | 82.7 ± 6.0% | 68.9 ± 11.7% | inactive |
| 40 | H | OCH₃ | H | OH | CH₂CH₂ | 52.4 ± 6.2% | 39.3 ± 3.8% | inactive |
| 41 | OCH₃ | H | H | OH | CH₂CH₂ | 49.8 ± 5.4% | 34.5 ± 4.3% | inactive |
| 44 | H | H | H | CH₃ | CH₂ | 44.2 ± 4.0% | 18.3 ± 6.4% | inactive |
| 45 | H | H | H | CH₃ | CH₂CH₂ | 47.9 ± 8.1% | 37.3 ± 10.0% | inactive |
| 46 | H | H | OCH₃ | CH₃ | CH₂CH₂ | 52.0 ± 7.1% | 42.2 ± 7.5% | inactive |
| 47 | H | H | H | CH₃ | CH=CH | 40.4 ± 1.3% | 27.4 ± 5.5% | inactive |
| 48 | H | OCH₃ | H | CH₃ | CH₂CH₂ | 29.9 ± 5.7% | 15.8 ± 9.0% | inactive |
| 49 | OCH₃ | H | H | CH₃ | CH₂CH₂ | 11.4 ± 3.3% | 6.3 ± 2.3% | inactive |
| 50 | | | | OH | CH₂CH(C₆H₆)₂ | 48.3 ± 4.1% | 67.9 ± 5.2% | inactive |
| 51 | | | | OH | CH₂C₁₀H₇ | 53.9 ± 5.1% | 62.9 ± 7.1% | inactive |
| 61 | | OCH₃ | H | | CH₂CH₂ | 50.9 ± 6.1% | 70.5 ± 4.7% | inactive |
| 64 | | OCH₃ | H | | CH₂CH₂ | 51.4 ± 4.8% | 69.4 ± 7.5% | inactive |
| 67 | | OCH₃ | H | | CH₂CH₂ | 52.8 ± 5.6% | 72.6 ± 4.3% | inactive |

[a]The ion current was induced by 2 μM ATP at the recombinant P2X receptors expressed in *Xenopus* oocytes and % inhibition of the ion current by 10 μM compound was measured for mouse P2X$_1$ and human P2X$_3$ receptors, respectively (mean ± SEM, n = 4). The accumulation of ethidium$^+$ was induced by 6 μM BzATP at the human P2X receptors expressed in HEK293 cells and % inhibition of the accumulation by 10 μM compound was measured (mean ± SEM, n = 3).

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A pyridine carboxylic acid-based compound represented by formula (I), isomers or pharmaceutically acceptable salt thereof:

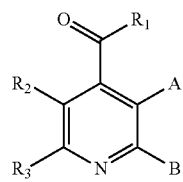
(I)

wherein, each of $R_1$, $R_2$ and $R_3$ is a substituent independently selected from the group consisting of hydrogen, hydroxy group, sulfonyl group, halogen, $C_1$-$C_6$ lower alkyl group, and $C_1$-$C_6$ lower alkoxy group;

A is

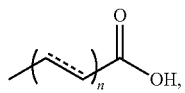
(A1)

wherein, n is 0; and
B is

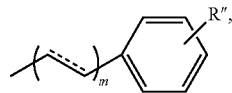
(B2)

wherein, R" is at least one substituent selected from the group consisting of hydrogen, hydroxy group, halogen, carboxylic acid, sulfonyl group, $C_1$-$C_6$ lower alkyl group, $C_1$-$C_6$ lower alkoxy group and $C_1$-$C_6$ lower alkyl ester group, and wherein m is 1, and (----) represents a single or double bond.

2. A pyridine carboxylic acid-based compound represented by formula (Ia), isomers or pharmaceutically acceptable salt thereof:

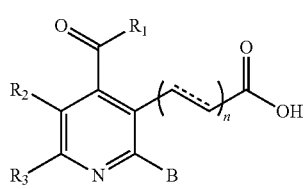
(Ia)

wherein, $R_1$, $R_2$, $R_3$, B and n have the same meaning as claim 1.

3. The compound according to claim 2, wherein each of $R_1$, $R_2$ and $R_3$ in the General formula (Ia) is a substituent selected from the group consisting of hydrogen, hydroxy group, sulfonyl group, methyl group, ethyl group, methoxy group and ethoxy group.

4. The compound according to 3, wherein the compound is selected from the group consisting of ethyl 3-(4-formyl-5-hydroxy-6-methylpyridin-3-yl) propanoic acid (13), 5-(2-carboxyethyl)-3-hydroxy-2-methylisonicotinic acid (14), (3-(2,2,8-trimethyl-4H-[1,3]dioxino[4,5-c]pyridin-5-yl) acrylic acid (15), 3-(5-hydroxy-4-(hydroxymethyl)-6-methylpyridin-3-yl)acrylic acid (16), 3-(4-Formyl-5-hydroxy-6-methylpyridin-3-yl)acrylic acid (17), 5-(2-Carboxyvinyl)-3-hydroxy-2-methylisonicotinic acid (18), N-Benzyl-1-(2,2,8-trimethyl-4H-[1,3]dioxino[4,5-c]pyridin-5-yl) methanamine (19), Ethyl 3-(benzyl((2,2,8-trimethyl-4H-[1,3]dioxino[4,5-c]pyridin-5-yl)methyl)amino)propanoate (20), 3-(Benzyl ((5-hydroxy-4-(hydroxymethyl)-6-methylpyridin-3-yl) methyl)amino) propanoic acid (21); 3-(Benzyl((4-formyl-5-hydroxy-6-methylpyridin-3-yl)methyl)amino) propanoic acid (22), 5-((Benzyl(2-carboxyethyl)amino)methyl)-3-hydroxy-2-methylisonicotinic acid (23); 3-(2-((2,5-Disulfophenyl)diazenyl)-4-formyl-5-hydroxy-6-methylpyridin-3-yl) propanoic acid (24), 3-(2-Carboxyethyl)-2-((2,5-di sulfophenyl)diazenyl)-5-hydroxy-6-methylisonicotinic acid (25), 3-(4-Formyl-5-hydroxy-6-methyl-2-((4-sulfophenyl) diazenyl)pyridin-3-yl) propanoic acid (26), 3-(2-carboxyethyl)-5-hydroxy-6-methyl-2-((4-sulfophenyl)diazenyl) isonicotinic acid (27), 4-((3-(2-carboxyethyl)-4-formyl-5-hydroxy-6-methylpyridin-2-yl)diazenyl)benzoic acid (28), 3-(2-carboxyethyl)-2-((4-carboxyphenyl)diazenyl)-5-hydroxy-6-methy lisonicotinic acid (29); 2-Benzyl-5-hydroxy-6-methyl-pyri dine-3,4-dicarboxylic acid (35), 5-Hydroxy-6-methyl-2-phenethyl-pyridine-3,4-dicarboxylic acid (36), 5-Hydroxy-2-[2-(4-methoxy-phenyl)ethyl]-6-methyl-pyridine-3,4-dicarboxylic acid (37), 5-Hydroxy-6-methyl-2-styryl-pyridine-3,4-dicarboxylic acid (38), 2-[2-(4-Carboxy-phenyl)-ethyl]-5-hydroxy-6-methyl-pyridine-3,4-dicarboxylic acid (39), 5-Hydroxy-2-[2-(3-methoxy-phenyl)-ethyl]-6-methyl-pyridine-3,4-dicarboxylic acid (40), 5-Hydroxy-2-[2-(2-methoxy-phenyl)-ethyl]-6-methyl-pyridine-3,4-dicarboxylic acid (41), 4-acetyl-2-benzyl-5-hydroxy-6-methylnicotinic acid (44), 4-acetyl-5-hydroxy-6-methyl-2-phenethylnicotinic acid (45), 4-acetyl-5-hydroxy-2-(4-methoxyphenethyl)-6-methylnicotinic acid (46), (E)-4-acetyl-5-hydroxy-6-methyl-2-styrylnicotinic acid (47), (E)-4-acetyl-5-hydroxy-2-(3-methoxystyryl)-6-methylnicotinic acid (48), (E)-4-acetyl-5-hydroxy-2-(2-methoxystyryl)-6-methylnicotinic acid (49), 3-(4-formyl-5-hydroxy-2-(4-methoxyphenethyl)-6-methylpyridin-3-yl)propanoic acid (61), (E)-3-(4-formyl-5-hydroxy-2-(4-methoxyphenethyl)-6-methylpyridin-3-yl)acrylic acid (64), 4-formyl-5-hydroxy-2-(4-methoxyphenethyl)-6-methylnicotinic acid (67); 5-Hydroxy-6-methyl-2-(naphthalene-1-ylmethyl)pyridine-3,4-dicarboxylic acid (50) and 2-(2,2-diphenylethyl)5-hydroxy-6-methylpyridine-3,4-dicarboxylic acid (51), isomers thereof and pharmaceutically acceptable salts thereof.

5. A pharmaceutical composition for treating chronic inflammatory a disease neurological pain disease or platelet aggregation disease, comprising a therapeutically effective amount of a compound represented by formula (I) of claim 1.

6. The pharmaceutical composition according to claim 5, wherein the disease treated is a chronic inflammatory disease.

7. The pharmaceutical composition according to claim 6, wherein the chronic inflammatory disease is selected from the group consisting of degenerative arthritis, rheumatoid arthritis, asthma, chronic obstructive pulmonary disease, and cystitis.

8. The pharmaceutical composition according to claim 5, wherein the disease treated is a neurological pain disease.

9. The pharmaceutical composition according to claim 8, wherein the neurological pain disease is selected from the group consisting of neuropathic pain, allodynia, diabetic neuropathy, spontaneous pain, irritability pain, phantom limb pain, and complex regional pain syndrome.

10. The pharmaceutical composition according to claim 5, wherein the disease treated is a platelet aggregation-associated disease.

11. The pharmaceutical composition according to claim 10, wherein the platelet aggregation disease is selected from the group consisting of arteriosclerosis, stroke, thrombosis, embolism, myocardial infarction, atherosclerosis, and peripheral blood circulatory disturbance.

* * * * *